(12) United States Patent
Cashman et al.

(10) Patent No.: US 9,403,800 B2
(45) Date of Patent: Aug. 2, 2016

(54) COMPOUNDS FOR INHIBITION OF CANCER CELL PROLIFERATION

(71) Applicants: John Cashman, San Diego, CA (US); Mark Mercola, San Diego, CA (US); Dennis Schade, San Diego, CA (US); Masanao Tsuda, San Diego, CA (US)

(72) Inventors: John Cashman, San Diego, CA (US); Mark Mercola, San Diego, CA (US); Dennis Schade, San Diego, CA (US); Masanao Tsuda, San Diego, CA (US)

(73) Assignee: ChemRegen, Inc., San Diego, CA (US)

(*) Notice: Subject to any disclaimer, the term of this patent is extended or adjusted under 35 U.S.C. 154(b) by 141 days.

(21) Appl. No.: 13/748,770

(22) Filed: Jan. 24, 2013

(65) Prior Publication Data
US 2013/0190258 A1    Jul. 25, 2013

Related U.S. Application Data

(60) Provisional application No. 61/632,515, filed on Jan. 24, 2012.

(51) Int. Cl.
| | |
|---|---|
| *C07D 403/12* | (2006.01) |
| *C07D 487/00* | (2006.01) |
| *A61K 31/635* | (2006.01) |
| *C07D 401/12* | (2006.01) |
| *C07D 413/12* | (2006.01) |
| *C07H 17/02* | (2006.01) |
| *A61K 45/06* | (2006.01) |
| *A61K 31/706* | (2006.01) |
| *A61K 31/4745* | (2006.01) |
| *A61K 31/513* | (2006.01) |
| *A61K 31/555* | (2006.01) |

(52) U.S. Cl.
CPC ......... *C07D 403/12* (2013.01); *A61K 31/4745* (2013.01); *A61K 31/513* (2013.01); *A61K 31/555* (2013.01); *A61K 31/635* (2013.01); *A61K 31/706* (2013.01); *A61K 45/06* (2013.01); *C07D 401/12* (2013.01); *C07D 413/12* (2013.01); *C07D 487/00* (2013.01); *C07H 17/02* (2013.01)

(58) Field of Classification Search
None
See application file for complete search history.

(56) References Cited

U.S. PATENT DOCUMENTS 6,867,204 B2 *    3/2005    Berger et al. ............ 514/211.09

OTHER PUBLICATIONS

Ettmayer, P. et al., Journal of Medicinal Chemistry, "Lessons Learned from Marketed and Investigational Prodrugs", 2004, vol. 47, No. 10, pp. 2393-2404.*
Stella, V. J., Expert Opinion Therapeutic Patents, "Prodrugs as therapeutics", 2004, vol. 14, No. 3, pp. 277-280.*
Testa, B., Biochemical Pharmacology, "Prodrug research: futile or fertile?", 2004, vol. 68, pp. 2097-2106.*
Wolff, M. E., Burger's Medicinal Chemistry and Drug Discovery, Fifth Edition, vol. I: Principles and Practice, pp. 975-977.*
CAPlus and Registry in STN entered Dec. 10, 2014, 79 page document.*

* cited by examiner

*Primary Examiner* — Layla Berry
*Assistant Examiner* — Bahar Craigo
(74) *Attorney, Agent, or Firm* — Angelo Castellino

(57) ABSTRACT

Methods and small molecule compounds for inhibition of cancer cell proliferation are provided. One example of a class of compounds that may be used is represented by the compound of Formula I or a pharmaceutically acceptable salt, N-oxide or solvate thereof, wherein A, B, D, E, F, G, I, J, R, $R_1$, $R_2$, $R_{2'}$, $R_3$, $R_4$, $R_5$, $R_6$, $R_7$, $R_8$, $R_9$ are as described herein.

6 Claims, 11 Drawing Sheets

COMPOUNDS FOR INHIBITION OF CANCER CELL PROLIFERATION

CROSS REFERENCE TO RELATED APPLICATION(S)

This application claims the benefit under 35 USC §119(e) of U.S. Provisional Patent Application Ser. No. 61/632,515, filed Jan. 24, 2012, the entire content of which is hereby incorporated by reference in its entirety for all purposes.

GRANT INFORMATION

This invention was not made with government support.

FIELD OF THE DISCLOSURE

The disclosure relates generally to small molecule compounds and more specifically to derivatives of sulfonamides and their use in cancer.

BACKGROUND OF THE DISCLOSURE

Cancer is a leading cause of cancer-related deaths in the United States. For example, colorectal cancer resulted in 51,370 deaths during 2010. Despite this prevalence, therapeutic options for cancer are currently limited to surgery, radiation, or chemotherapy. These non-specific therapies are effective for early stage but not for metastatic cancer and frequently cause untoward gastrointestinal and hematologic side effects. Further, monoclonal antibody treatments specific for cancer are reserved for patients with advanced disease because these therapies provide limited clinical benefit, are cost prohibitive and require intravenous delivery. Thus, there is a major unmet medical need for the development of selective, inexpensive and non-toxictargeted treatments for human cancer.

Therapies targeting protein components of dysregulated signal transduction pathways can be efficacious anti-cancer therapies with minimal adverse effects. The initiation and progression of colon, breast, prostate, pancreatic and other human tumors has been shown to depend on mutations in β-catenin (β-cat) itself or upstream regulators, leading to stabilization and increased levels of β-cat that in turn activate genes involved in tumor maintenance and proliferation. Direct inhibition of Wnt/β-cat is an oncology target but simply blocking the ubiquitously expressed β-cat, however, has adverse consequences on cell adhesion and tissue integrity in normal tissues. Compounds that potently and selectively inhibit the nuclear availability of TCF proteins that binds β-cat and is required for its activation of downstream Wnt target genes in a number of human cancers could be a useful therapeutic. Compounds that selectively inhibit the Wnt pathway very far downstream of normal physiological function of the Wnt pathway could decrease human cancer cell proliferation in vitro and inhibit cancer proliferation in vivo. Further, compounds that work very far downstream of normal physiological function of Wnt will work with minimal side effects, thus showing novel therapeutic utility. These targeted Wnt inhibitors may also be used in combination with traditional cancer chemotherapies including 5-fluoruracil, oxaliplatin, or irinotecan. Combination therapy of Wnt molecular pathway inhibitors with chemotherapeutics will allow for lower effective doseages resulting in fewer adverse side effects.

Certain efforts have focused with limited success on decreasing cellular pools of β-cat because of decreased adhesion and tissue integrity in normal tissues. A compound that inhibits the Wnt pathway far downstream and remote of β-cat could potently and selectively increasephosphorylated TCF proteins in the nucleus without affecting β-cat levels outside the nucleus. Accordingly, the effects on normal tissue would be minimal. A compound that potently and selectively inhibits β-cat availability in the nucleus could decrease cellular proliferation in cancer. This is in contrast to the well-established Wnt inhibitors of the multi-protein destruction complex (e.g., IWR-1), that have no effect on colorectal and other cancer cell proliferation. Thus, a compound that selectively inhibits Wnt by increasing TCF protein phosphorylation would possess several characteristics that render them distinct and superior to other reported Wnt inhibitors: i). inhibition of the Wnt pathway at the transcriptional level provides not only inhibition of Wnt target genes but also preserves upstream Wnt signaling, ii). they would not interfere with cellular adhesion and result in maintenance of normal tissue structure in contrast to most other previously reported Wnt inhibitors. Targeting TCF provides several advantages over other target proteins in the Wnt pathway because its action is at the nuclear level similar to transcriptional co-activator antagonists. Targeting TCF also blocks the Wnt pathway completely. Phosphorylation of TCF proteins inhibits transcriptional activities of them. TCF4 and LEF1 are transcriptional activators and stimulation of phosphorylation results in inhibition of transcription. HIPK2 is the kinase that does this phosphorylation and thus, developing activators of HIPK2 provides a rapid and efficient means of identifying potent anti-cancer agents and compounds that could decrease the proliferation of cancer and cancer stem cells.

The Wnt pathway is dysfunctional in several other cancers including colon cancer, prostate cancer, breast cancer, ovarian cancer, uterine cancer, liver cancer, malignant melanoma, pancreatic cancer and gastric cancer and glioblastoma and other brain cancers. Developmental work has been done in several institutions to capitalize on the promise of Wnt inhibitors in cancer but problems associated with interference of normal physiological function of Wnt has not been addressed. Thus, the invention disclosed herein identifies and validates new paradigms to identify new biological pathways and targets that can be used to inhibit cancer cell growth and proliferation.

In addition to cancer, the Wnt pathway plays a pivotal role in neurochemistry and is involved in neurogenesis and neuronal disease. As such, small molecules described herein may modulate neuronal diseases and be of utility in inhibiting diseases of neurological origin.

Emerging evidence suggests that Wnt signaling regulates crucial aspects of a number of cancer tumor initiation and progression. The Wnt pathway is dependent on the cellular level of β-cat. Under normal physiologic conditions, the majority of β-cat resides in the cytoplasm and is maintained at a low level through degradation that is regulated by a multi-protein "destruction" complex containing axin. Upon Wnt stimulation, Axin translocates to the cell membrane to interact with LRP5 and Dvl. Dvl becomes phosphorylated and subsequently inhibits GSK3β-kinase phosphorylation of β-cat thereby resulting in the accumulation of non-phosphorylated β-cat in the cytoplasm. This non-phosphorylated β-cat then translocates to the nucleus where it interacts with the TCF/LEF family of transcription factors, binds to Wnt DNA response elements of target genes, and recruits the transcriptional machinery to enhance gene expression. The Wnt target genes include genes that promote cellular proliferation, metabolism, cellular migration, and differentiation. Additionally, several protein components of the Wnt pathway are frequently mutated and/or over-expressed in many types of cancer. β-cat and several protein components of the multi-protein degradation complex including APC and Axin2 have been found to be mutated in patients with colon cancer. These mutations all prevent β-cat degradation leading to enhanced cellular β-cat levels and subsequent activation of Wnt target gene expression. β-cat (non-mutated) is also over-expressed in several cancers. Recent studies have also highlighted the importance of alternatively-spliced TCF isoforms in cancer. These TCF isoforms have divergent effects on Wnt target gene activity. For example, truncated TCF isoforms often cannot interact with β-cat and thus, act as dominant negative transcription factors blocking recruitment of β-cat and the associated transcriptional machinery to the Wnt gene promoters. In contrast, another TCF isoform that has a novel activation function leads to activation of Wnt target genes. An analysis of TCF isoform expression in both normal and cancerous colon tissue indicated that relative TCF isoform expression changes with tumor progression influence the Wnt target gene activity. As an attractive oncology target, several new small molecules, existing drugs, natural compounds and biologics have been reported to act as inhibitors of the Wnt signaling pathway. These agents either act as β-cat/TCF antagonists, molecules stabilizing the multi-protein destruction complex (i.e., IWR-1) transcriptional co-activators modulators, Dvl PDZ-domain antagonists, or other unknown targets. But these agents cause toxicity. Compounds targeting the Wnt pathway far downstream should avoid the untoward-side effects from influencing the cytoplasmic effects of the Wnt pathway and focus on inhibiting only the transcription of Wnt target genes leading to decreased cellular proliferation and migration. Such a compound is 1 and refined analogs.

Compound 1 inhibited the canonical Wnt pathway independently of β-cat. This is apparent because: a) 1 does not affect β-cat levels or localization, b) 1 potently blocks β-cat activity induced either by GSK3β inhibitor BIO, by a mutation in APC in SW480 cells, or by over-expression of constitutive active form of β-cat, and c) 1 did not affect interaction of β-cat with TCF proteins or co-activators (CBP and p300). Together, these results indicated that 1 inhibited canonical Wnt signaling independent of β-cat stabilization, localization, and its interaction with its co-activators. This is in contrast to previously characterized Wnt inhibitors that block various points in the signaling pathway. Instead of affecting β-cat, 1 inhibited the Wnt pathway through HIPK2 activation based on the following observations; a) 1 caused a mobility shift of over-expressed TCF3, LEF1, and TCF4, that are phosphorylated by HIPK2, and 1 induced phosphorylation of TCF3, b) 1 induced a mobility shift of HIPK2 and siRNA for HIPK2 rescued inhibition of Wnt reporter gene expression by 1, indicating that 1 exerts its activity through HIPK2, c) consistent with previous observation in which HIPK2 phosphorylated TCF proteins to prevent their association with β-cat and chromatin, 1 decreased recruitment of TCF4 to its target site in the endogenous c-MYC promoter, and d) over-expression of HIPK2 enhanced 1 activity on the Wnt pathway. Consistent with their modes of action (TCF4 is an activator whereas TCF3 is a repressor)—the Wnt reporter responded by decreasing (for TCF4) and increasing (TCF3) luciferase activity by 1; combination with HIPK2 further enhanced this interaction. Finally, the physiological relevance for compound 1 induced HIPK2 activation during development was confirmed by evaluating anterior/posterior marker genes expression. Vent2 and Otx2 are regulated by TCF3 during anteroposterior axis specification in xenopus embryo and HIPK2 antagonizes them via phosphorylation of TCF3. Xenopus embryos incubated with compound 1 showed reduced anterior marker gene Otx2, whereas anterior and ventral expression domain of Vent2 was expanded. These phenotypes are very similar to embryos with TCF3-knockout and contrast to those of HIPK2-knockout. Together, the observations show that compound 1 activates HIPK2 to remove TCF proteins from their target DNA via phosphorylation.

SUMMARY OF THE DISCLOSURE

In one aspect, the disclosure provides a compound of Formula I:

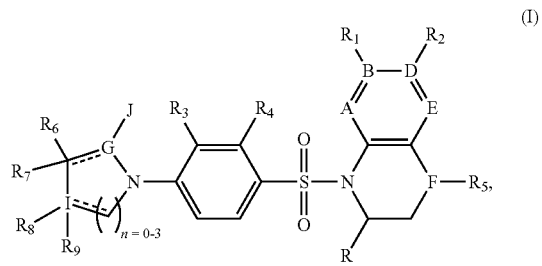

or a pharmaceutically acceptable salt, N-oxide or solvate thereof, wherein:

A, B, D, E are independently Carbon, Nitrogen, Oxygen or Sulfur. F, G, I can be independently Carbon, Oxygen, Sulfur, or Nitrogen. J can be keto (O=), hydroxyl, hydrogen, ($C_1$-$C_6$)alkyl, aryl, cycloalkyl, cycloheteroalkyl, heteroaryl. R, $R^1$, $R^2$, $R^3$, $R^4$, $R^5$, $R^6$, $R^7$, $R^8$, $R^9$=H, alkyl, aryl, halo, O-alkyl, O-aryl, N-alkyl, N,N-dialkyl, N-aryl, N,N-diaryl, cycloalkyl, cycloheteroalkyl, heteroaryl.

R is independently substituted hydrogen, ($C_1$-$C_6$)alkyl, aryl, halogen, $CF_3$, $C_2F_5$, O-alkyl, N-alkyl O-aryl or a moiety forming a salt;

$R_1$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt;

$R_2$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt;

$R_3$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt;

$R_4$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt; or unsubstituted phenyl, substituted or unsubstituted pyridine, wherein phenyl or pyridine is optionally independently substituted with 1 to 3 substituents;

$R_5$ is independently substituted hydrogen, ($C_1$-$C_6$)alkyl aryl, halogen, hydroxyl, $CF_3$, $C_2F_5$, O-alkyl, O-aryl, cycloalkyl($C_1$-$C_6$), alkyl($C_1$-$C_6$)amine, alkyl cyclic ($C_1$-$C_6$) amine, alkyl ($C_1$-$C_6$) N,N-dialkylamino, alkyl ($C_1$-$C_6$)aryl amine, cycloheteroalkyl, heteroaryl, methylcycloalkyl($C_1$-$C_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independently substituted;

$R_6$ and $R_7$ are independently substituted hydrogen, keto (=O), ($C_1$-$C_6$)alkyl, aryl, halogen, $CF_3$, $C_2F_5$, hydroxyl, O-alkyl, O-aryl, amine, cyclic amine, N,N-dialkylamino, aryl amine, cycloalkyl($C_1$-$C_6$), alkyl($C_1$-$C_6$)amine, alkyl cyclic ($C_1$-$C_6$)amine, alkyl($C_1$-$C_6$) N,N-dialkylamino, alkyl ($C_1$-

$C_6$)aryl amine, cycloheteroalkyl, heteroaryl, N,N-diarylamino, or a moiety forming a salt; or unsubstituted phenyl, substituted or unsubstituted pyridine, wherein phenyl or pyridine is optionally independently substituted with 1 to 3 independent substituents, O-alkyl, O-aryl, amino, N-alkylamino, N-arylamino, or hydroxyl or amino prodrug moieties, $R_6$, $R_7$, $R_8$ and $R_9$ re independently substituted S and R isomeric forms and racemic forms, $R_8$ and $R_9$ are independently substituted hydrogen, keto (=O), ($C_1$-$C_6$)alkyl, aryl, halogen, $CF_3$, $C_2F_5$, hydroxyl, O-alkyl, O-aryl, amine, cyclic amine, N,N-dialkylamino, aryl amine, cycloalkyl($C_1$-$C_6$), alkyl($C_1$-$C_6$)amine, alkyl cyclic ($C_1$-$C_6$)amine, alkyl($C_1$-$C_6$) N,N-dialkylamino, alkyl ($C_1$-$C_6$)aryl amine, cycloheteroalkyl, heteroaryl, N,N-diarylamino, or a moiety forming a salt; or unsubstituted phenyl, substituted or unsubstituted pyridine, wherein phenyl or pyridine is optionally independently substituted with 1 to 3 independent substituents, or hydroxyl or amino prodrug moieties, In another aspect the disclosure provides methods for inhibiting cancer cell proliferation by contacting the cell with a compound of Formula I.

In another aspect the disclosure provides methods for inhibiting cancer cell proliferation, comprising contacting cancer cells with a sulfonamide-based compound of structure I in the form of a free base or a pharmaceutically acceptable salt, hydrate, solvate or N-oxide thereof, wherein A, B, D, E, F, G, J, R, $R_1$-$R_9$, are as described above.

In another aspect the disclosure provides methods for inhibiting cancer cell proliferation, migration, and promoting apoptosis in vivo comprising contacting cancer cells with a sulfonamide-based compound of structure I as described above, in the form of a free base or a pharmaceutically acceptable salt, hydrate, solvate or N-oxide thereof.

DETAILED DESCRIPTION OF THE DISCLOSURE

Figure 1:
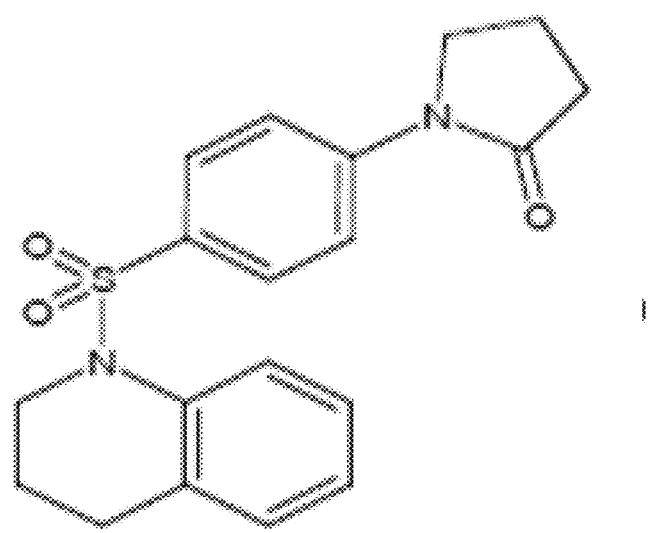
FIG. 1 shows the chemical structure for Compound 1.

The following terms, definitions and abbreviations apply. Abbreviations used herein have their conventional meaning within the chemical and biological arts.

The term "lipophilic" refers to moieties having an affinity for lipids and other fat-like substances, tending to combine with, and capable of dissolving, them.

The term "cancer" refers to cells undergoing uncontrolled proliferation.

The term "cancer stem cell" refers to a cancer cell with traits associated with normal stem cells.

The term "cancer cell proliferation" refers to a series of events involved in the uncontrolled increase in the cell division rate of cancer cells, where the cells have lost specific structural, functional, and biochemical cell-cycle checkpoints.

The term "patient" refers to organisms to be treated by the methods of the disclosure. Such organisms include, but are not limited to, humans. In the context of the disclosure, the term "subject" generally refers to an individual who will receive or who has received treatment described below (e.g., administration of the compounds of the disclosure, and optionally one or more additional therapeutic agents).

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclopropyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—, —$CH_2CH=CHCH_2$—, —$CH_2CCCH_2$—, —$CH_2CH_2CH$($CH_2CH_2CH_3$)$CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclopropyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" refers to a carbon or heteroatom.

The term "oxo or keto" as used herein means an oxygen that is double bonded to a carbon atom.

The terms "heterocycle" and "heterocyclic" refer to a monovalent unsaturated group having a single ring or multiple condensed rings, from 1 to 8 carbon atoms and from 1 to 4 heteroatoms, for example, nitrogen, sulfur or oxygen within the ring.

The term "methylthio" refers to a moiety —S—CH$_3$.

The term "sulfonamide" refers to compound A shown below, as well as to the other

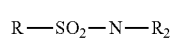

A moieties derived from compound A: The terms "furyl," "tetrahydrofuryl," and "pyridyl" refer to radicals formed by removing one hydrogen from the molecules of furan, tetrahydrofuran, and pyridine, respectively.

The terms "alkyl amine" and "cyclic amine" refer to alkanes or cycloalkanes, respectively, having one hydrogen substituted by a primary, secondary or tertiary amino group, as well as to the moieties and radicals derived from such amines.

The term "alkyl amide" refers to alkanes, having one hydrogen substituted by a primary, secondary or tertiary amino group.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")═NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$O CH$_3$, and the like).

The term "alkoxy" refers to the moiety —O-alkyl, wherein alkyl is as defined above. Examples of alkoxy structures that are within the purview of the definition include, but are not limited to, (C$_1$-C$_6$)alkoxy radicals, such as methoxy, ethoxy, propoxy, isopropoxy, butoxy, iso-butoxy, sec-butoxy, tert-butoxy, pentoxy, 3-pentoxy, or hexyloxy.

Similar to the substituents described for alkyl radicals above, exemplary substituents for aryl and heteroaryl groups (as well as their divalent derivatives) are varied and are selected from, for example: halogen, —OR', —NR'R'', —SR', -halogen, —SiR'R''R''', —OC(O)R', —C(O)R', —CO2R', —C(O)NR'R'', —OC(O)NR'R'', —NR''C(O)R', —NR'—C(O)NR''R''', —NR''C(O)OR', —NR—C(NR'R''R''')=NR'', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R'', R''' and R'''' are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula -T-C(O)—(CRR')q-U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)r-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), or silicon (Si).

An "aminoalkyl" as used herein refers to an amino group covalently bound to an alkylene linker. The amino group is —NR'R'', wherein R' and R'' are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties: (A)-OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the disclosure may exist as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When the disclosed compounds contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

The term "pharmaceutically acceptable salt" refers to salts that may be used where the compounds used in the methods of the disclosure are sufficiently basic or acidic to form stable nontoxic acid or base salts. Examples of pharmaceutically acceptable salts include organic acid addition salts formed with acids which form a physiological acceptable anion, for example, oxalate, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by treating a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by and are intended to be within the scope of the disclosure.

Certain compounds of the disclosure possess centers of chirality (e.g., asymmetric carbon atoms), optical or chiral centers or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another. It will be apparent to one skilled in the art that certain compounds of the disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each center of chirality (e.g., a asymmetric carbon center). Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure.

The compounds of the disclosure may also contain unnatural proportions of atomic isotopes at one or more atoms that constitute such compounds. For example, the compounds may be radiolabeled with radioactive isotope, such as for example, tritium ($^{3}$H), iodine-125 ($^{125}$I) or carbon-14 ($^{14}$C). All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

In addition to salt forms, the disclosure provides compounds, which are in a prodrug form. Prodrugs of the compounds described herein are those compounds that readily undergo chemical or metabolism-mediated changes under physiological conditions to provide the compounds of the disclosure. For example, a phosphate or other ester moiety or other prodrug moiety may be independently attached to $R_1$-$R_9$). Additionally, prodrugs can be converted to the compounds of the disclosure by chemical or biochemical methods in an ex vivo environment. For example, prodrugs can be slowly converted to the compounds of the disclosure when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" in reference to a particular disease includes prevention of the disease.

The disclosure also provides articles of manufacture comprising packaging material and a pharmaceutical composition contained within said packaging material, wherein said packaging material comprises a label which indicates that said pharmaceutical composition can be used for treatment of disorders and wherein said pharmaceutical composition comprises a compound according to the disclosure.

The disclosure also provides pharmaceutical compositions comprising at least one compound in an amount effective for treating a disorder, and a pharmaceutically acceptable vehicle or diluent. The compositions of the disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like. Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed pharmaceutical compositions may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally or with cavitands (i.e., Captisol).

In addition to primates, such as humans, a variety of other mammals can be treated according to the method of the disclosure. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The pharmaceutical compositions for the administration of the compounds of this embodiment either alone or in combination with other agents, (e.g., chemotherapeutic), may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of disease. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether β-cyclodextrin, Captisol, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, for example, in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the disclosure are employed. For purposes of this application, topical application shall include mouthwashes and gargles.

In the methods described herein, an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was dosed at 20 mg/kg/day while another was effective at about 30 mg/kg/day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or once or twice per day. There may be a period of no administration followed by another regimen of administration. Administration of the compounds may be closely associated with the schedule of a second agent of administration.

It will be understood, however, that the specific dose level and frequency of dosage for any particular patient may be varied and will depend upon a variety of factors including the potency of the specific compound employed, the metabolic stability and length of action of that compound, the age, body weight, general health, gender, diet, mode and time of administration, rate of excretion, drug combination, the severity of the particular condition, and the host undergoing therapy.

Thus, in one embodiment the disclosure provides a compound of Formula I:

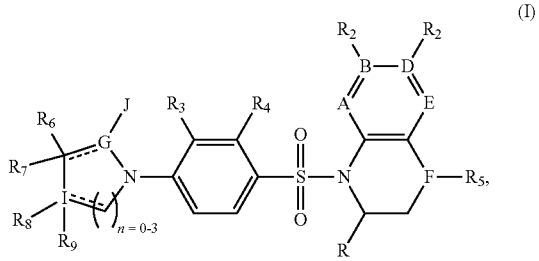

or a pharmaceutically acceptable salt, N-oxide or solvate thereof, wherein:

A, B, D, E are independently Carbon, Nitrogen, Oxygen or Sulfur. F, G, I can be independently Carbon, Oxygen, Sulfur, or Nitrogen. J can be keto (O=), hydroxyl, hydrogen, ($C_1$-$C_6$)alkyl, aryl, cycloalkyl, cycloheteroalkyl, heteroaryl. R, $R_1$, $R_2$, $R_3$, $R_4$, $R_5$, $R_6$, $R_7$, $R_8$, $R_9$=H, alkyl, aryl, halo, O-alkyl, O-aryl, N-alkyl, N,N-dialkyl, N-aryl, N,N-diaryl, cycloalkyl, cycloheteroalkyl, heteroaryl.

R is independently substituted hydrogen, ($C_1$-$C_6$)alkyl, aryl, halogen, $CF_3$, $C_2F_5$, O-alkyl, N-alkyl O-aryl or a moiety forming a salt;

$R_1$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt;

$R_2$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt;

$R_3$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt;

$R_4$ is independently substituted hydrogen, ($C_1$-$C_6$)alkyl, aryl, halogen, $CF_3$, $C_2F_5$, O-alkyl, O-aryl, amine, cyclic amine, aryl amine or a moiety forming a salt; or unsubstituted phenyl, substituted or unsubstituted pyridine, wherein phenyl or pyridine is optionally independently substituted with 1 to 3 substituents;

$R_5$ is independently substituted hydrogen, ($C_1$-$C_6$)alkyl aryl, halogen, $CF_3$, $C_2F_5$, hydroxyl, O-alkyl, O-aryl, cycloalkyl($C_1$-$C_6$), alkyl($C_1$-$C_6$)amine, alkyl cyclic($C_1$-$C_6$) amine, alkyl($C_1$-$C_6$) N,N-dialkylamino, alkyl ($C_1$-$C_6$)aryl amine, cycloheteroalkyl, heteroaryl, methylcycloalkyl($C_1$-$C_6$), methylaryl, methylcycloheteroalkyl, methylheteroaryl, methylcyclopropyl, or a moiety forming a salt; or unsubstituted phenyl, substituted or unsubstituted pyridine, wherein phenyl or pyridine is optionally independently substituted with 1 to 3 independently substituted;

$R_6$ and $R_7$ are independently substituted hydrogen, keto (=O), ($C_1$-$C_6$)alkyl, aryl, halogen, $CF_3$, $C_2F_5$, hydroxyl, O-alkyl, O-aryl, amine, cyclic amine, N,N-dialkylamino, aryl amine, cycloalkyl($C_1$-$C_6$), alkyl($C_1$-$C_6$)amine, alkyl cyclic ($C_1$-$C_6$)amine, alkyl($C_1$-$C_6$) N,N-dialkylamino, alkyl ($C_1$-$C_6$)aryl amine, cycloheteroalkyl, heteroaryl, N,N-diarylamino, or a moiety forming a salt; or unsubstituted phenyl, substituted or unsubstituted pyridine, wherein phenyl or pyridine is optionally independently substituted with 1 to 3 independent substituents, O-alkyl, O-aryl, amino, N-alkylamino, N-arylamino, or hydroxyl or amino prodrug moieties, $R_6$, $R_7$, $R_8$ and $R_9$ are independently substituted S and R isomeric forms and racemic forms, $R_8$ and $R_9$ are independently substituted hydrogen, keto (=O), ($C_1$-$C_6$)alkyl, aryl, halogen, $CF_3$, $C_2F_5$, hydroxyl, O-alkyl, O-aryl, amine, cyclic amine, N,N-dialkylamino, aryl amine, cycloalkyl($C_1$-$C_6$), alkyl($C_1$-$C_6$)amine, alkyl cyclic ($C_1$-$C_6$)amine, alkyl($C_1$-$C_6$) N,N-dialkylamino, alkyl ($C_1$-$C_6$)aryl amine, cycloheteroalkyl, heteroaryl, N,N-diarylamino, or a moiety forming a salt; or unsubstituted phenyl, substituted or unsubstituted pyridine, wherein phenyl or pyridine is optionally independently substituted with 1 to 3 independent substituents, or $C_6$-$C_9$ hydroxyl or amino prodrug moieties including phosphate, or aliphatic esters or amino acid esters, amidines or saccharides;

In another aspect the disclosure provides a compound of Formula I, wherein R, $R_1$-$R_9$ is independently substituted hydrogen; is O-alkyl; substituted or unsubstituted phenyl, F, Cl, Br, or I; $C_1$-$C_6$-alkyl optionally substituted by

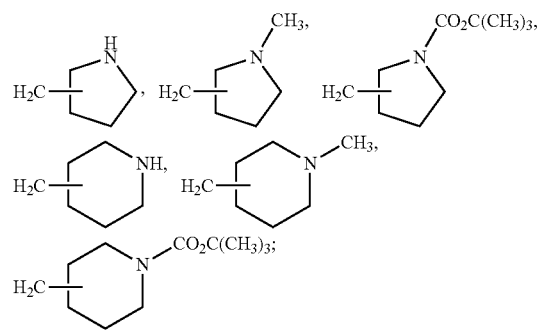

In another aspect the disclosure provides compounds of Formula I, wherein the pharmaceutically acceptable salt is the salt of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid
(D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), or undecylenic acid.

In another aspect the disclosure provides methods for inhibiting cancer cells by contacting the cancer cells or mammals with a compound of Formula I.

In another aspect the disclosure provides methods for inhibiting cancer cell growth by contacting the cancer cells or mammals with a compound of Formula I, further comprising inhibiting cancer cell growth by inhibiting the Wnt pathway.

In another aspect the disclosure provides methods for inhibiting cancer cell growth by contacting cancer cells with a compound of Formula I, further comprising contacting the cells with a stimulator of HIPK2 that increases phosphorylation of TCF proteins and decreases transcription of Wnt target genes. In another aspect the disclosure provides methods for inhibiting cancer cell proliferation by contacting the cancer cells with a compound of Formula I, comprising contacting the cells with compounds that phosphorylate TCF4 and LEF1. TCF4 and LEF1 are transcriptional activators and stimulation of phosphorylation results in inhibition of transcription.

In another aspect the disclosure provides methods for inhibiting cancer cell proliferation by contacting the cancer cells with a compound of Formula I, comprising contacting the cells with compounds that stabilize protein p53.

In another aspect the disclosure provides methods for inhibiting cancer cell proliferation by contacting the cancer cells with a compound of Formula I, comprising contacting the cells with compounds that inhibits MDM2 and stabilizes p53 protein.

Those skilled in the art may determine the optimal time of contacting the cancer cells or mammal and with the disclosed compounds described herein required to achieve the optimal results. As a guideline, the period of contact may be between about 24 hours and about 192 hours, or for example, between about 48 hours and about 144 hours.

The cancer cells suitable for use in the disclosed methods may be derived from a patient's own tissue. This would enhance compatibility of the compounds with the patient. In this context it should be noted that cancer cells can include cancer cells derived from a person's own tissue, stem cells, and the like.

In another aspect the disclosure provides methods of treating or preventing cancer or a cancerous condition, the method including introducing a compound when treated in accordance with the disclosed methods to a subject.

The cellular and molecular events regulating the Wnt pathway in cancer are important to understanding the development and function of anti-cancer agents. Potent, selective agents that increase phosphorylation of TCF4 is important for the development of cellular therapies for the treatment of cancer disease including colon cancer, prostate cancer, breast cancer, pancreatic cancer, glioblastoma and other brain cancers. and other cancers. Accordingly, compounds described in the disclosure find particular use in inhibiting cancer cell proliferation, migration and increasing apoptosis and the like by use alone or in the presence of other anti-cancer agents.

In one aspect, the compounds of the disclosure are used to screen for targets of their action. For example, competitive analyses can be performed using compounds with known targets. Such targets include, for example, but not limited to Wnt, MEF2C; β-cat; TCF/LEF; Smad2, Smad3; Smad4 (binding partners of the above proteins are also potential targets since they would modulate activity); p38, p53, MDM2 and SIAH2 and components of the signaling that activate MEF2C; components of the Wnt pathway, such as Frizzled proteins, CaMK, Axin, Dishevelled, APC, GSK3, FRAP; Calmodulin.

EXAMPLES

The embodiments of the disclosure may be further illustrated by the following non-limiting examples.

Example 1

Biological Assays

"Hit" 1 (FIG. 1) was identified as a Wnt inhibitor in a high-throughput screen of a library of 74,000 compounds using a cell-based Wnt-luciferase reporter assay as a readout of Wnt transcriptional activity. Compound 1 inhibited Wnt transcriptional activity in a dose-dependent manner with $EC_{50}$ of ~25 nM similar to the well-characterized Wnt inhibitor, IWR-1. Wnt transcriptional activity was monitored in HEK-293T cells using a luciferase-based Wnt reporter (SuperTOPFlash) stimulated by Wnt3a conditioned media. The selectivity of 1 was confirmed in secondary assays by the observation that 25, a structural analog of 1 did not inhibit Wnt transcriptional activity. The selectivity of 1 for the Wnt pathway was shown because 1 did not alter the transcriptional activity of either the NF-B or the TGF-signaling pathways, two other predominant cellular signaling pathways.

Compound 1 inhibited the endogenous Wnt pathway as determined by a decrease in mRNA levels of canonical Wnt target genes, Cyclin D1 (CCND1), Axin2 (AXIN2), and c-Myc (c-MYC) in both HEK293T and SW480 colorectal cells. IWR-1 also decreased mRNA expression of these genes whereas IQ-1, an activator of the Wnt pathway, enhanced mRNA expression. Previous studies highlighted the importance of Wnt pathway signaling in promoting cellular differentiation. Accordingly, the physiological relevance of the Wnt inhibitory functions of 1 was shown by the effect of this compound on the morphology of xenopus embryos during embryonic development. Treatment with 1 during the mid-blastula transition inhibited posterior development of these embryos similar to treatment with IWR-1. Xenopus embryos incubated with 1 showed decreased anterior marker gene Otx2, whereas anterior and ventral expression domain of Vent2 was expanded. Vent2 and Otx2 are regulated by TCF3 during anteroposterior axis specification in xenopus embryos and HIPK2 antagonizes them through phosphorylation of TCF3. These phenotypes are very similar to embryos with TCF3-knockout and contrast to those of HIPK2-knockout.

Together, the observations indicate that compound 1 activates HIPK2 to remove TCF proteins from their target DNA via phosphorylation.

Thus, 1 affects the anterior-posterior axis formation because the Wnt pathway has been shown to be critical for this developmental phase by working through stem-like cells in xenopus. Together, these data show 1 potently and selectively inhibits canonical Wnt signaling in both cell-based assays and in vivo development.

Figure 2:
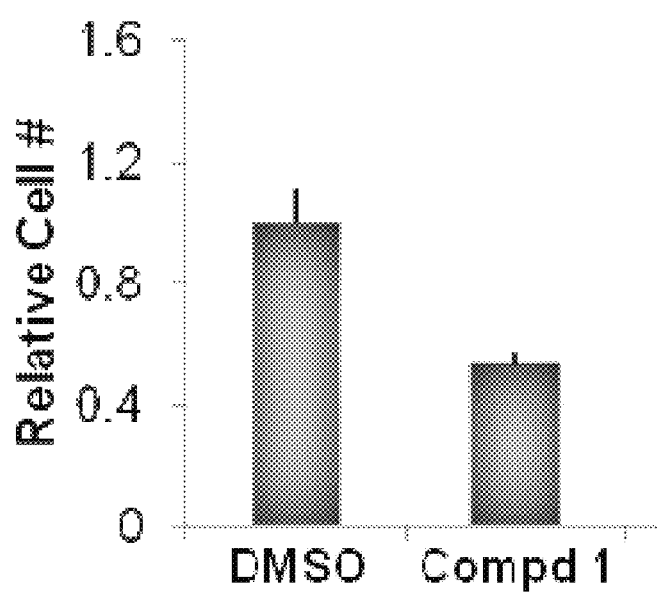
FIG. 2 shows that Compound 1 inhibits the cellular proliferation of the SW480 colorectal cancer model cell line.
Figure 3:
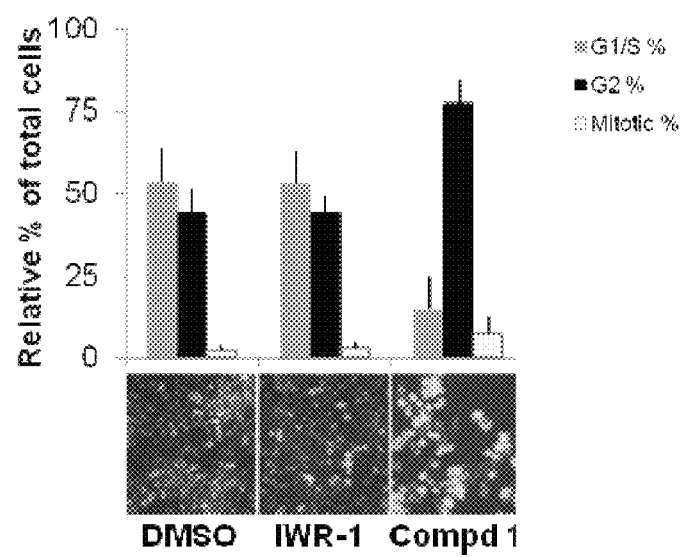
FIG. 3 shows data that Compound 1 disrupts the SW480 cell cycle.

Previous studies have shown that the Wnt signaling pathway drives cellular proliferation of a number of cancers through up-regulation of genes for several proteins crucial for cell division including Cyclin D1, c-Myc, etc. and treatment of cancer cells with 1 or analogs decreases cellular proliferation. Accordingly, we examined the effect of 1 and analogs on cell proliferation of human cancer cell lines. As shown in Table 2 or FIG. 2 for colon cancer cell line SW480, 1 and analogs significantly inhibited cancer cell proliferation. In contrast, several commercially available Wnt inhibitors did not influence human cancer cell proliferation. The results were confirmed by studying the effects of 1 on SW480 human colon cell cycle determined by cell images captured by InCell 1000. SW480 cells cultured in the presence of 1 showed significantly more cells in G2 and less in G1/S phases indicating that 1 affected the G2 checkpoint (FIG. 3). Ki67 protein levels in the SW480 cells treated with 1 were elevated suggesting these cells were G2-arrested and not exiting the cell cycle. In contrast, IWR-1 did not alter either the rate of SW480 cell proliferation or cell cycle, suggesting IWR-1 and 1 inhibited the Wnt pathway by different mechanisms. Treatment with 1 or potent analogs did not have any affect on normal human fibroblast cells whereas 1 and certain analogs potently inhibited rapidly dividing cancer cells. 1 and potent analogs selectively inhibit rapidly dividing cells or cycling cells and do not have any affect on normal or non-dividing cells.

Figure 4:
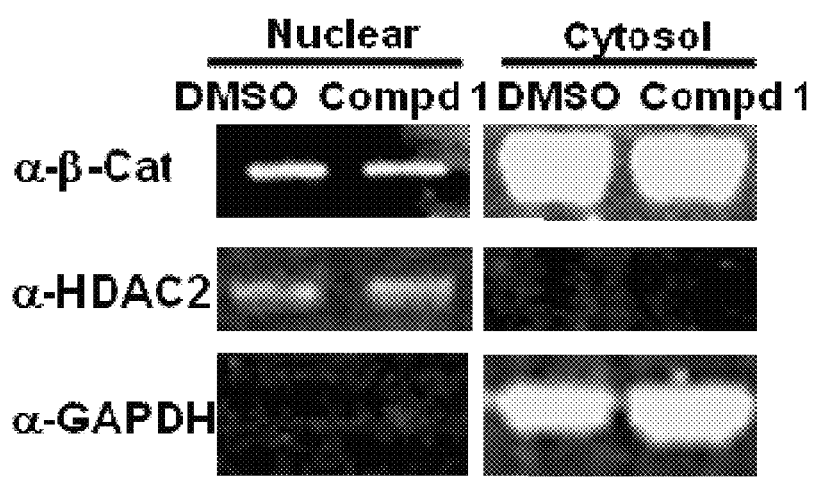
FIG. 4 shows data that -cat protein levels or cellular localization are not affected by Compound 1.
Figure 5:
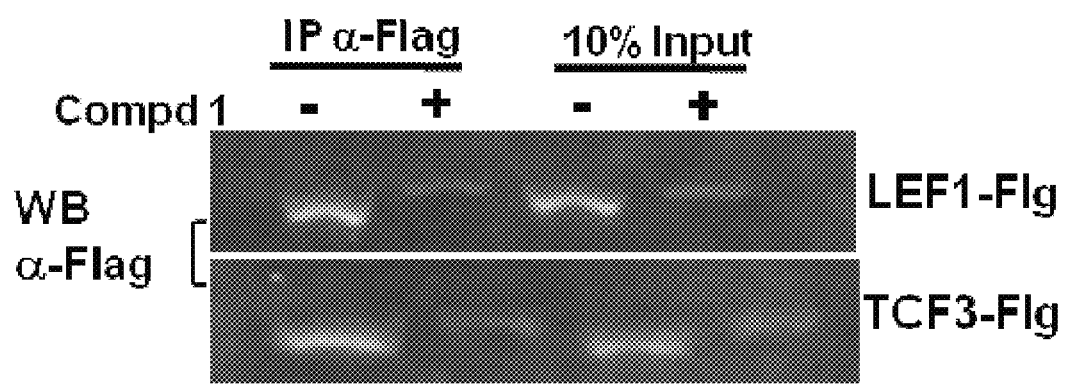
FIG. 5 shows data that Compound 1 increased molecular weight of TCF protein on the basis of immunoprecipitation (IP).
Figure 6:
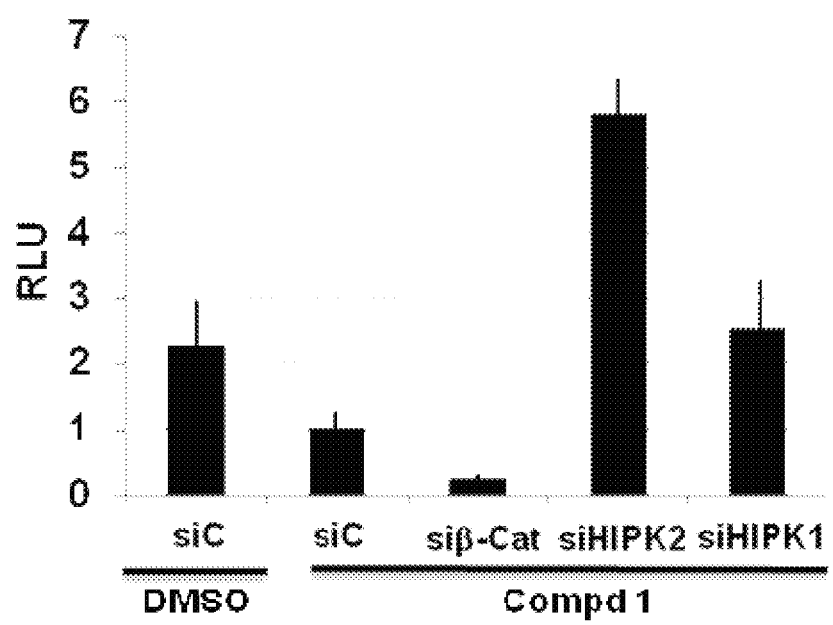
FIG. 6 shows data that HIPK2 silencing reverses Compound 1 inhibition of the Wnt pathway.

Treatment of SW480 cells with 1 for up to 24 hours did not change β-cat protein levels in SW480 cells (FIG. 4). We also examined the effect of 1 on the cellular localization of β-cat by treating SW480 cells with 1 for 24 hours followed by cellular fractionization. Neither β-cat protein levels nor localization were affected by 1 in SW480 cells. In HEK293T cells treated with 1, nuclear extracts immunoprecipitated with selective antibodies showed decreased levels of over-expressed TCF proteins (i.e., TCF4, LEF1, TCF3). 1 caused a mobility shift of over-expressed LEF-1, TCF3 and TCF4. The functional activity of TCF proteins is regulated by various modifications including phosphorylation. Phosphorylation of TCF proteins by the kinase HIPK2 causes disassociation of TCF proteins from their target promoters. Thus, we studied the effect of 1 and other analogs on functional activity of the TCF proteins in the presence or absence of HIPK2. TCF4 and LEF1 transcriptional activity on the Wnt-luciferase reporter were decreased by both HIPK2 over-expression and subsequent 1 treatment whereas TCF3 activity was enhanced consistent with previous studies that phosphorylation by HIPK2 inhibits activities of LEF1 and TCF4, but enhances TCF3. HIPK2 down-regulation using siRNA rescued inhibition of the Wnt-luciferase reporter transcriptional activity by 1 and analogs but siRNA targeted to HIPK1, a closely related protein, had no effect (FIG. 6). Phosphorylation of target proteins by HIPK2 has been previously shown to result in dissociation of TCF proteins from their target DNA. Using chromatin immunoprecipitation, treatment with 1 or analogs decreased recruitment of TCF4 from the cMyc 3' enhancer 14-fold relative to DMSO control indicating that 1 modulates TCF4 recruitment to its target enhancer without affecting the interaction between TCF4 and β-cat (FIG. 5). This further shows that 1 inhibits Wnt transcriptional activity by decreasing the amount of active TCFs available for stimulation of transcription of Wnt target genes. HIPK2 has been shown to sensitize cells to apoptosis. We observed an increase in apoptotic HEK293 cells upon treatment with 1 (see below). Together these results suggest that 1 exerts its effects on Wnt signaling via HIPK2.

The disclosed compounds inhibit the Wnt pathway likely involving the inhibition of ubiquitination of p53 by MDM2 by blocking the p53/MDM2 protein-protein interaction. Thus, assays involving competition of disclosed compounds with p53/MDM2 interaction represent a selective means of identifying novel anti-cancer agents. Binding of the disclosed compounds to the p53-binding domain of MDM2 is tested by isothermal titration calorimetry (or other means) using the purified recombinant p53-binding domain of MDM2 and a dose range (low nM to 500 nM) compound 15. The IC50 value of 15 or other disclosed compounds is directly related to the potency as an anti-cancer agent.

The disclosed compounds inhibit the Wnt pathway likely involving the inhibition of the E3-Ubiquitin-Ligase class of proteins. Binding of the E3-Ubiquitin Ligases and compound 15 is tested by isothermal titration calorimetry using the purified recombinant RING-domain of MDM2 and a dose range (low nM to 5000 nM) of compound 15. The potency of compound 15 on the enzyme activity of several different E3-Ubiquitin Ligases including MDM2 and SIAH2 using a standard ubiquitination-enzyme assay and in vitro translated E3-Ubiquitin ligases can be measured by determining the IC50 value. The IC50 value of 15 or other disclosed compounds is directly related to the potency as an anti-cancer activity.

Medicinal chemical refinement of "hit" 1 was undertaken to improve its potency, maintain non-toxicity, increase water solubility and improve bioavailability. The SAR refinement of functional activity of "hit" 1 on the inhibition of the Wnt pathway was determined using a cell-based Wnt-luciferase reporter assay (described above). with Renilla Luciferase was used as a normalization for transfection efficiency. 6-8 hours after transfection, transfected HEK293A cells were treated with 1 and each analog for 12 hours. Both firefly and renilla luciferase activities were measured using a plate reader. A library of compounds was tested to obtain an SAR for 1. Compound 1 and its analogs are synthesized by a two step synthesis, Scheme 1.

From preliminary SAR, the lactam ring was very sensitive to modification (e.g., expansion to a six-membered ring gave a loss of potency) although certain modifications were beneficial. We focused on the tetrahydroquinoline portion of the molecule and analogs were synthesized and tested (Table 1). The tetrahydroquinoline ring appeared to be necessary for functional activity. The tetrahydroisoquinoline ring maintained potency equal to 1. The SAR potency follows the following tetrahydroquinoline substitution: MeO=Cl>Me, >H>>F. This suggests that more strongly electron donating groups (i.e., $NMe_2$) will be even more potent and after salt formation, improve the water solubility of 1. Thus additional analogs were synthesized. From the data obtained thus far, certain analogs were more potent than the 6-methoxytetrahydroquinoline analog and helped to improve the pharmaceutical properties of the molecule. From the results thus far, the 6-chloro (compound 2) and 6-methoxy (compound 3) showed potent inhibition of Wnt.

Example 2

General Synthetic Procedures for Obtaining Compounds of Formula I

The sulfonamide-based compounds of general structure I:

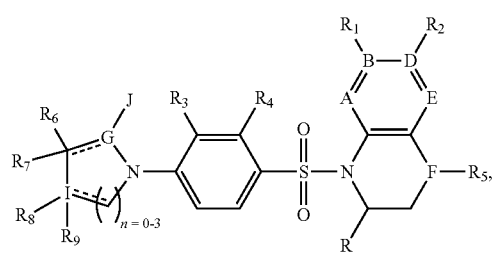

may be synthesized according to the following Schemes:

Scheme 1: General Synthetic Procedure for synthesis of aryl sulfonamides of structure I.

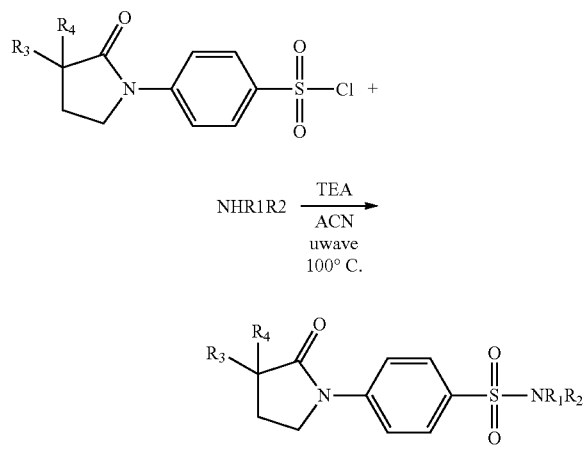

Compound I:

To a microwave vial, 1 equiv. of the sulfonyl chloride, 1.5 equiv. of the appropriate amine, 1.2 equiv. of triethylamine were added to acetonitrile (0.4 M). The vial was sealed and heated at 100° C. and microwaved for 20 min. The reaction mixture was diluted with dichloromethane and washed 2× water, 1× brine. The organic was dried over $Na_2SO_4$. The crude mixture was purified by silica gel chromatography.

Scheme 2: General Synthetic Procedure for synthesis of pyrollidine or pyrazolidine aryl sulfonamides of structure I.

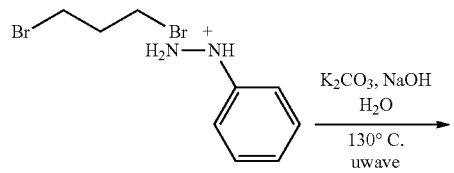

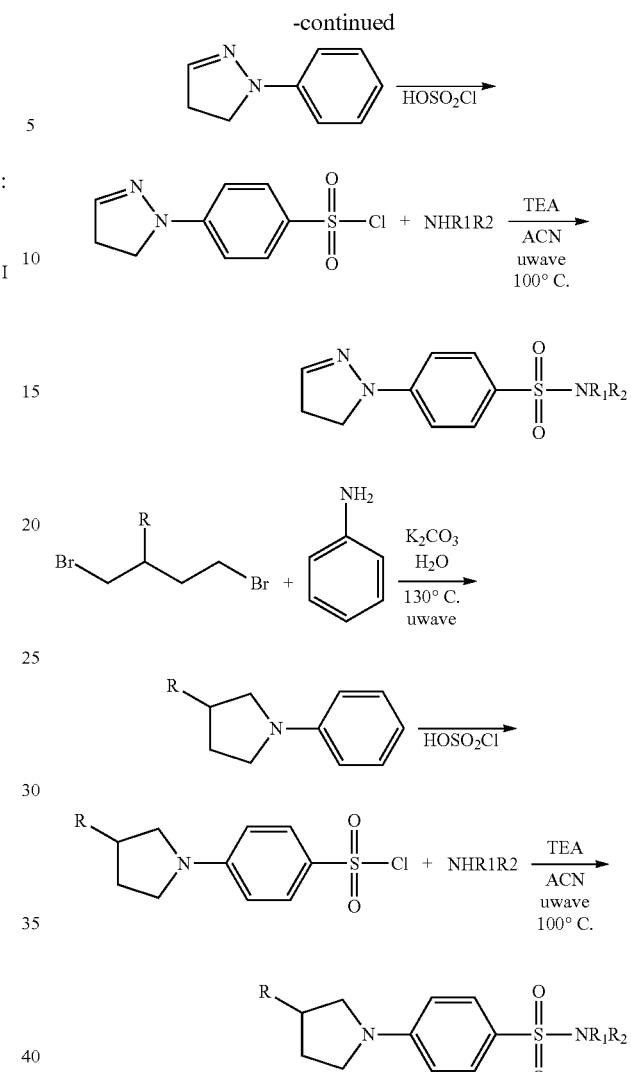

Compound I.

10 mmol of phenylhydrazine hydrochloride or aniline, 10 mmol 1,3-dibromopropane or 1,4-dibromobutane, 10 mmol potassium carbonate and 10 mL water were added to a microwave vial and heated at 130 C for 30 min. The mixture was extracted 4× ethyl acetate. The organic layers were combined, dried over $Na_2SO_4$ and concentrated in vacuo to give a yellow residue. The crude mixture was purified by flash chromatography (25% EtOAc/Hex). Next, 10 mmol of phenylpyrollidine or phenylpyroazolidine was added to 10 eq of chlorosulfonic acid. The reaction was stirred overnight at room temperature. The reaction mixture was stopped by slow addition to ice. The aqueous mixture was extracted with 4×DCM. The organic layers were combined, dried over $Na_2SO_4$ and concentrated in vacuo to give an off white solid. The sulfonyl chloride was used without any further purification. Then, to a microwave vial, 1 equiv. of the sulfonyl chloride, 1.5 equiv. of the appropriate amine, 1.2 equiv. of triethylamine were added to acetonitrile (0.4 M). The vial was sealed and heated at 100 C and microwaved for 20 min. The reaction mixture was diluted with dichloromethane and washed 2× water, 1× brine. The organic was dried over $Na_2SO_4$. The crude mixture was purified by silica gel chromatography.

Scheme 3. Wnt Sulfonamides of Structure I.

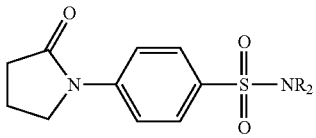

1. NR$_2$ = 1,2,3,4-tetrahydroquinoline
2. NR$_2$ = 6-methyl-1,2,3,4-tetrahydroquinoline
3. NR$_2$ = decahydroquinoline
4. NR$_2$ = 2-methyl-1,2,3,4-tetrahydroquinoline
5. NR$_2$ = 6-chloro-1,2,3,4-tetrahydroquinoline
6. NR$_2$ = 6-fluoro-1,2,3,4-tetrahydroquinoline
7. NR$_2$ = 6-methoxy-1,2,3,4-tetrahydroquinoline
8. NR$_2$ = 6-trifluoromethyl-1,2,3,4-tetrahydroquinoline
9. NR$_2$ = 6-t-butyl-1,2,3,4-tetrahydroquinoline
10. NR$_2$ = 6-(N,N-dimethylamino)-1,2,3,4-tetrahydroquinoline
11. NR$_2$ = 7-methyl-1,2,3,4-tetrahydroquinoline
12. NR$_2$ = 1,2,3,4-tetrahydroisoquinoline
13. NR$_2$ = 6-methyl-1,2,3,4-tetrahydroisoquinoline
14. NR$_2$ = 7-methyl-1,2,3,4-tetrahydroisoquinoline
15. NR$_2$ = 1-methyl-1,2,3,4-tetrahydroquinolxaline
16. NR$_2$ = 3,4-dihydro-2H-1,4-benzoxazine
17. NR$_2$ = aniline
18. NR$_2$ = o-anisidine
19. NR$_2$ = 2-trifluoromethoxyaniline
20. NR$_2$ = 1-aminonaphthalene
21. NR$_2$ = piperidine
22. NR$_2$ = 2-methylpiperidine
23. NR$_2$ = N-propylaniline
24. NR$_2$ = N-butylaniline

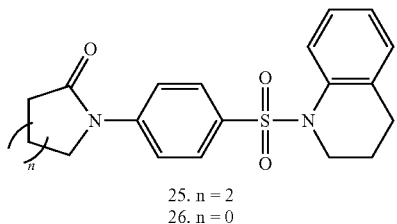

25. n = 2
26. n = 0

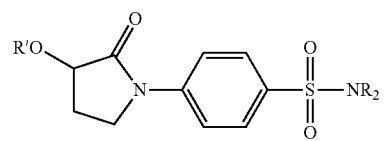

27. R' = CH$_3$
    NR$_2$ = 1-methyl-1,2,3,4-tetrahydroquinoxaline
28. R' = H
    NR$_2$ = 1-methyl-1,2,3,4-tetrahydroquinoxaline
29. R' = CH$_3$
    NR$_2$ = 2-methyl-1,2,3,4-tetrahydroquinoline
30. R' = CH$_3$
    NR$_2$ = 1,2,3,4-tetrahydroquinoline

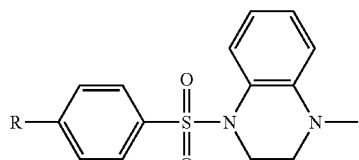

31. R = pyrollidine
32. R = pyrazolidine
33. R = pyrazole
34. R = 3-hydroxypyrrolidine

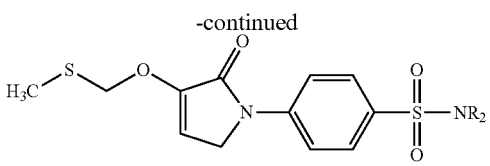

35. NR$_2$ = 1-methyl-1,2,3,4-tetrahydroquinoxaline

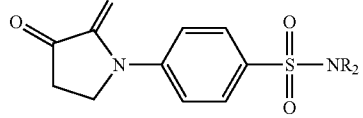

36. NR$_2$ = 1-methyl-1,2,3,4-tetrahydroquinoxaline

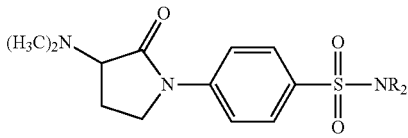

37. NR$_2$ = 1-methyl-1,2,3,4-tetrahydroquinoxaline

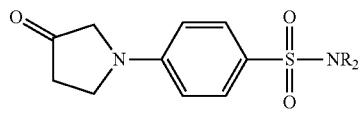

38. NR$_2$ = 1-methyl-1,2,3,4-tetrahydroquinoxaline

NMR and MS data for compounds of general structure I.

1-(4-(3,4-dihydroquinolin-1(2H)-ylsulfonyl)phenyl)pyrrolidin-2-one, 1

ESI/MS: m/z=356.42 [M].
$^1$H NMR (CDCl$_3$): 1.60-1.70 (m, 2H), 2.12-2.22 (m, 2H), 2.44 (t, J=6.6 Hz, 2H), 2.63 (t, J=6.6 Hz, 2H), 3.78-3.86 (m, 4H), 6.97-7.19 (m, 2H), 7.54 (d, J=9.1 Hz, 2H), 7.69 (d, J=9.1 Hz, 2H), 7.77 (d, J=8.8 Hz, 2H).

1-(4-(6-methyl-3,4-dihydroquinolin-1(2H)-ylsulfonyl)phenyl)pyrrolidin-2-one, 2

ESI/MS: m/z=370.02 [M].
$^1$H NMR (CDCl$_3$): 1.56-1.65 (m, 2H), 2.14-2.21 (m, 2H), 2.29 (s, 3H), 2.39 (t, J=6.6 Hz, 2H), 2.64 (t, J=6.6 Hz, 2H), 3.76-3.88 (m, 4H), 6.79 (bs, 1H), 6.98 (d, J=9.1 Hz, 1H), 7.55 (d, J=9.1 Hz, 2H), 7.65-7.72 (m, 4H).

1-(4-(octahydroquinolin-1(2H)-ylsulfonyl)phenyl)pyrrolidin-2-one, 3

ESI/MS: m/z=362.75 [M].
$^1$H NMR (CDCl$_3$): 0.87-1.77 (m, 14H), 2.14-2.24 (m, 2H), 2.37-2.49 (m, 1H), 2.65 (t, J=6.6 Hz, 2H), 3.89 (t, J=6.6 Hz, 2H), 4.04-4.11 (m, 1H), 7.72-7.82 (m, 4H).

1-(4-(2-methyl-3,4-dihydroquinolin-1(2H)-ylsulfonyl)phenyl)pyrrolidin-2-one, 4

ESI/MS: m/z=370.54
$^1$H NMR (CDCl$_3$): 1.3 (d, J=6.6 Hz, 3H), 1.26-1.40 (m, 2H), 1.77-1.88 (m, 2H), 2.13-2.23 (m, 2H), 2.35-2.45 (m, 2H), 2.64 (t, J=8.3 Hz 2H), 3.82-3.87 (m, 2H), 4.32-4.42 (m,

1H), 6.95-6.97 (m, 1H), 7.07-7.12 (m, 1H), 7.19-7.25 (m, 1H), 7.46 (d, J=9.0 Hz, 2H), 7.66 (d, J=9.0 Hz, 2H), 7.72-7.77 (m, 1H).

1-(4-(6-chloro-3,4-dihydroquinolin-1(2H)-ylsulfonyl)phenyl)pyrrolidin-2-one, 5

ESI/MS: m/z=390.86

$^1$H NMR (CDCl$_3$): 1.51-1.66 (m, 2H), 2.15-2.25 (m, 2H), 2.43 (t, J=6.1 Hz 2H), 3.77-3.81 (m, 2H), 3.86 (t, J=8.3 Hz 2H), 3.82-3.87 (m, 2H), 6.97-6.99 (m, 1H), 7.12-7.16 (m, 1H), 7.56 (d, J=9.0 Hz, 2H), 7.73 (d, J=9.0 Hz, 2H), 7.74-7.77 (m, 1H).

1-(4-(6-fluoro-3,4-dihydroquinolin-1(2H)-ylsulfonyl)phenyl)pyrrolidin-2-one, 6

ESI/MS: m/z=374.28

$^1$H NMR (CDCl$_3$): 1.58-1.65 (m, 2H), 2.15-2.25 (m, 2H), 2.40 (t, J=6.6 Hz 2H), 2.65 (t, J=8.5 Hz 2H), 3.77-3.81 (m, 2H), 3.86 (t, J=7.2 Hz, 2H), 6.67-6.72 (m, 1H), 6.86-6.93 (m, 1H), 7.53 (d, J=9.0 Hz, 2H), 7.71 (d, J=9.0 Hz, 2H), 7.74-7.78 (m, 1H).

1-(4-(6-methoxy-3,4-dihydroquinolin-1(2H)-ylsulfonyl)phenyl)pyrrolidin-2-one, 7

ESI/MS: m/z=386.58

$^1$H NMR (CDCl$_3$): 1.53-1.62 (m, 2H), 2.14-2.25 (m, 2H), 2.35 (t, J=6.9 Hz 2H), 2.64 (t, J=8.5 Hz 2H), 3.75-3.78 (m, 2H), 3.78 (s, 3H), 3.86 (t, J=7.2 Hz 2H), 6.50-6.51 (m, 1H), 6.73-6.77 (m, 1H), 7.52 (d, J=9.1 Hz, 2H), 7.67-7.72 (m, 3H).

1-(4-(6-(trifluoromethyl)-3,4-dihydroquinolin-1(2H)-ylsulfonyl)phenyl)-pyrrolidin-2-one, 8

ESI/MS: m/z=424.28

$^1$H NMR (CDCl$_3$): 1.67-1.75 (m, 2H), 2.13-2.25 (m, 2H), 2.56-2.67 (m, 4H), 3.83-3.89 (m, 4H), 7.38-7.42 (m, 1H), 7.61 (d, J=8.8 Hz, 2H), 7.75 (d, J=8.8 Hz, 2H), 7.90-7.93 (m, 1H), 8.00-8.04 (m, 1H).

1-(4-(6-tert-butyl-3,4-dihydroquinolin-1(2H)-ylsulfonyl)phenyl)pyrrolidin-2-one

ESI/MS: m/z=412.82

$^1$H NMR (CDCl$_3$): 1.30 (s, 9H), 1.59-1.68 (m, 2H), 2.14-2.24 (m, 2H), 2.48 (t, J=6.6, 2H), 2.64 (t, J=8.3, 2H), 3.77-3.80 (m, 2H), 3.86 (t, J=6.9, 2H), 6.98 (d, J=2.5 Hz, 1H), 7.19 (dd, J=2.5 Hz and 8.8 Hz, 1H), 7.59 (d, J=9.1 Hz, 2H), 7.67 (d, J=8.8 Hz, 1H), 7.70 (d, J=9.1 Hz, 2H).

1-(4-(7-methyl-3,4-dihydroquinolin-1(2H)-ylsulfonyl)phenyl)pyrrolidin-2-one, 11

ESI/MS: m/z=370.35

$^1$H NMR (CDCl$_3$): 1.57-1.65 (m, 2H), 2.14-2.24 (m, 2H), 2.35 (s, 3H), 2.40 (t, J=6.9, 2H), 2.64 (t, J=8.5, 2H), 3.77-3.80 (m, 2H), 3.85 (t, J=6.9, 2H), 6.88 (s, 2H), 7.56 (d, J=9.0 Hz, 2H), 7.62 (s, 1H), 7.69 (d, J=9.0 Hz, 2H).

1-(4-(3,4-dihydroisoquinolin-2(1H)-ylsulfonyl)phenyl)pyrrolidin-2-one, 12

ESI/MS: m/z=356.20

$^1$H NMR (CDCl$_3$): 2.16-2.27 (m, 2H), 2.66 (t, J=8.0 Hz 2H), 2.90 (t, J=6.0 Hz 2H), 3.36 (t, J=6.0 Hz 2H), 3.90 (t, J=7.0 Hz 2H), 4.25 (s, 2H), 7.00-7.15 (m, 4H) 7.82 (s, 4H).

1-(4-(6-methyl-3,4-dihydroisoquinolin-2(1H)-ylsulfonyl)phenyl)pyrrolidin-2-one

ESI/MS: m/z=370.54

$^1$H NMR (CDCl$_3$): 2.21-2.26 (m, 2H), 2.28 (s, 3H), 2.66 (t, J=7.7 Hz, 2H), 2.89 (t, J=6.2 Hz, 2H), 3.34 (t, J=6.1 Hz, 2H), 3.89 (m, J=7.2 Hz 2H), 4.21 (s, 2H), 6.88-6.96 (m, 3H), 7.81 (s, 4H).

1-(4-(7-methyl-3,4-dihydroisoquinolin-2(1H)-ylsulfonyl)phenyl)pyrrolidin-2-one

ESI/MS: m/z=370.54

$^1$H NMR (CDCl$_3$): 2.16-2.26 (m, 2H), 2.28 (s, 3H), 2.66 (t, J=7.7 Hz, 2H), 2.88 (t, J=6.1 Hz, 2H), 3.34 (t, J=5.8 Hz, 2H), 3.89 (t, J=6.9 Hz 2H), 4.21 (s, 2H), 6.88-6.96 (m, 3H), 7.81 (s, 4H).

1-(4-(4-methyl-3,4-dihydroquinoxalin-1(2H)-ylsulfonyl)phenyl)pyrrolidin-2-one, 15

ESI/MS: m/z=372.65

$^1$H NMR (CDCl$_3$): 2.14-2.24 (m, 2H), 2.64 (t, J=8.5 Hz, 2H), 2.66 (s, 3H), 2.88 (t, J=5.5 Hz, 2H), 3.83-3.89 (m, 4H), 6.55-6.58 (m, 1H), 6.65-6.71 (m, 1H), 6.55-6.58 (m, 1H), 7.50 (d, J=9.0 Hz, 2H), 7.59-7.62 (m, 1H), 7.69 (d, J=9.0 Hz, 2H).

1-(4-(2H-benzo[b][1,4]oxazin-4(3H)-ylsulfonyl)phenyl)pyrrolidin-2-one, 16

ESI/MS: m/z=358.25

$^1$H NMR (CDCl$_3$): 2.14-2.24 (m, 2H), 2.65 (t, J=8.5 Hz, 2H), 2.72-2.75 (m, 2H), 3.83-3.90 (m, 4H), 6.77-6.80 (m, 1H), 6.90-6.96 (m, 1H), 7.03-7.09 (m, 1H), 7.60 (d, J=9.0 Hz, 2H), 7.74 (d, J=9.0 Hz, 2H), 7.83-7.86 (m, 1H).

4-(2-oxopyrrolidin-1-yl)-N-phenylbenzenesulfonamide, 17

ESI/MS: m/z=316.68 [M].

$^1$H NMR (CDCl$_3$): 2.16-2.22 (m, 2H); 2.65 (t, J=8.5 Hz, 2H); 3.85 (t, J=8.5 Hz, 2H); 7.04-7.23 (m, 4H); 7.72 (s, 2H).

N-(2-methoxyphenyl)-4-(2-oxopyrrolidin-1-yl)benzenesulfonamide, 18

ESI/MS: m/z=346.88 [M]

$^1$H NMR (CDCl$_3$): 2.11-2.23 (m, 2H), 2.61 (t, J=8.5 Hz, 2H), 3.65 (s, 3H), 3.82 (t, J=8.5 Hz, 2H), 6.71 (d, J=9.3 Hz, 1H), 6.86 (t, J=9.1 Hz, 1H), 6.97-7.0. (m, 1H), 7.04 (bs, NH), 7.50 (d, J=9.3 Hz, 1H), 7.66-7.74 (m, 3H).

4-(2-oxopyrrolidin-1-yl)-N-(2-(trifluoromethoxy) phenyl)benzenesulfonamide, 19

ESI/MS: m/z=400.62[M].
$^1$H NMR (CDCl$_3$): 2.13-2.23 (m, 2H), 2.63 (t, J=8.5 Hz, 2H), 3.85 (t, J=8.5 Hz, 2H), 7.04 (bs, NH), 7.05-7.25 (m, 3H), 7.65-7.77 (m, 4H).

N-(naphthalen-1-yl)-4-(2-oxopyrrolidin-1-yl)benzenesulfonamide, 20

ESI/MS: m/z=366.55 [M]
$^1$H NMR (CDCl$_3$): 2.10-2.21 (m, 2H), 2.62 (t, J=6.6 Hz, 2H), 3.80 (t, J=6.6 Hz, 2H), 7.08 (bs, NH), 7.32-7.47 (m, 3H), 7.63-7.92 (m, 8H).

1-(4-(piperidin-1-ylsulfonyl)phenyl)pyrrolidin-2-one, 21

ESI/MS: m/z=308.75 [M].
$^1$H NMR (CDCl$_3$): 1.36-1.44 (m, 2H), 1.60-1.67 (m, 4H), 2.16-2.26 (m, 2H), 2.66 (t, J=6.6 Hz, 2H), 2.96 (t, J=6.6 Hz, 2H), 3.90 (t, J=6.6 Hz, 2H), 7.70-7.82 (m, 4H).

1-(4-(2-ethylpiperidin-1-ylsulfonyl)phenyl)pyrrolidin-2-one, 22

ESI/MS: m/z=336.75 [M].
$^1$H NMR (CDCl$_3$): 0.87 (t, J=7.1 Hz, 3H), 1.36-1.44 (m, 2H), 1.60-1.67 (m, 9H), 2.14-2.24 (m, 2H), 2.64 (t, J=6.6 Hz, 2H), 2.96 (t, J=6.6 Hz, 2H), 3.74 (d, J=14.0 Hz, 1H), 3.89 (t, J=6.6 Hz, 2H), 7.72-7.82 (m, 4H).

4-(2-oxopyrrolidin-1-yl)-N-phenyl-N-propylbenzenesulfonamide, 23

ESI/MS: m/z=358.29 [M]
$^1$H NMR (CDCl$_3$): 0.90 (t, J=7.4 Hz, 3H), 1.38-1.48 (m, 2H), 2.16-2.27 (m, 2H), 2.67 (t, J=8.4 Hz 2H), 3.47-3.52 (m, 2H), 3.86 (t, J=6.9 Hz, 2H), 7.02-7.06 (m, 2H), 7.28-7.32 (m, 2H), 7.56 (d, J=9.0 Hz, 2H), 7.74 (d, J=9.0 Hz, 2H).

N-butyl-4-(2-oxopyrrolidin-1-yl)-N-phenylbenzenesulfonamide, 24

ESI/MS: m/z=372.67 [M]
$^1$H NMR (CDCl$_3$): 0.86 (t, J=7.2 Hz, 3H), 1.30-1.43 (m, 4H), 2.18-2.27 (m, 2H), 2.67 (t, J=7.7 Hz 2H), 3.47-3.55 (m, 2H), 3.89 (t, J=7.2 Hz, 2H), 7.02-7.06 (m, 2H), 7.28-7.32 (m, 2H), 7.56 (d, J=9.0 Hz, 2H), 7.74 (d, J=9.0 Hz, 2H).

1-(4-(3,4-dihydroquinolin-1(2H)-ylsulfonyl)phenyl) piperidin-2-one, 25

ESI/MS: m/z=370.25 [M+]

N-(4-(3,4-dihydroquinolin-1(2H)-ylsulfonyl)phenyl)-N-methylacetamide, 26

ESI/MS: m/z=344.82 [M]
$^1$H NMR (CDCl$_3$): 1.62-1.68 (m, 2H), 1.94 (bs, 3H), 2.44 (t, J=9.0, 2H), 3.29 (s, 3H), 3.79-3.83 (m, 2H), 7.01 (d, J=2.2 Hz, 1H), 7.17 (dd, J=2.2 Hz and 8.8 Hz, 1H), 7.27 (d, J=8.3 Hz, 2H), 7.63 (d, J=8.3 Hz, 2H), 7.73 (d, J=8.8 Hz, 1H).

3-methoxy-1-(4-(4-methyl-3,4-dihydroquinoxalin-1 (2H)-ylsulfonyl)phenyl)-pyrrolidin-2-one, 27

ESI/MS: m/z=401.88 [M+H]
$^1$H NMR (CDCl$_3$): 2.06-2.17 (m, 1H), 2.45-2.56 (m, 1H), 2.65 (s, 3H), 2.87 (t, J=5.0, 2H), 3.60 (s, 3H), 3.67-3.75 (m, 1H), 3.84 (t, J=5.0, 2H), 3.80-3.88 (m, 1H), 4.08 (t, J=7.4 Hz, 1H), 6.55 (dd, J=8.3 Hz and J=1.1 Hz, 1H), 6.65-6.70 (m, 1H), 7.04-7.10 (m, 1H), 7.50 (d, J=9.1 Hz, 2H), 7.59 (dd, J=8.0 Hz and J=1.3 Hz, 1H), 7.70 (d, J=9.1 Hz, 2H).

3-hydroxy-1-(4-(4-methyl-3,4-dihydroquinoxalin-1 (2H)-ylsulfonyl)phenyl)-pyrrolidin-2-one, 28

ESI/MS: m/z=387.52 [M+H]
$^1$H NMR (CDCl$_3$): 2.05-2.19 (m, 1H), 2.58-2.68 (m, 1H), 2.66 (s, 3H), 2.88 (t, J=5.2, 2H), 3.24 (bs, 1H), 3.70-3.83 (m, 2H), 3.84 (t, J=5.2, 2H), 4.49 (t, J=9.3 Hz, 1H), 6.56 (d, J=8.0 Hz, 1H), 6.68 (t, J=7.4 Hz, 1H), 7.08 (t, J=7.4 Hz, 1H), 7.51 (d, J=8.8 Hz, 2H), 7.60 (d, J=8.5 Hz, 1H), 7.70 (d, J=8.8 Hz, 2H).

3-methoxy-1-(4-(2-methyl-3,4-dihydroquinolin-1 (2H)-ylsulfonyl)phenyl)-pyrrolidin-2-one, 29

ESI/MS: m/z=400.68 [M+H]
$^1$H NMR (CDCl$_3$): 1.29 (d, J=6.3 Hz, 3H), 1.26-1.41 (m, 1H), 1.75-1.90 (m, 2H), 2.05-2.17 (m, 1H), 2.32-2.56 (m, 2H), 3.61 (s, 3H), 3.67-3.75 (m, 1H), 3.80-3.91 (m, 1H), 4.07 (t, J=7.2 Hz, 1H), 4.32-4.40 (m, 1H), 6.94-6.98 (m, 1H), 7.07-7.13 (m, 1H), 7.19-7.24 (m, 1H), 7.46 (d, J=9.1 Hz, 2H), 7.69 (d, J=8.8 Hz, 2H), 7.73 (d, J=8.3 Hz, 1H).

1-(4-(3,4-dihydroquinolin-1(2H)-ylsulfonyl)phenyl)-3-methoxypyrrolidin-2-one, 30

ESI/MS: m/z=386.25 [M+H]; $^1$H NMR (CDCl$_3$): 1.61-1.70 (m, 2H), 2.05-2.17 (m, 1H), 2.45 (t, J=6.9 Hz, 2H), 2.45-2.56 (m, 1H), 3.60 (s, 3H), 3.68-3.76 (m, 1H), 3.78-3.89 (m, 3H), 4.07 (t, J=7.7 Hz, 1H), 6.97-7.00 (m, 1H), 7.04-7.09 (m, 1H), 7.15-7.21 (m, 1H), 7.58 (d, J=8.8 Hz, 2H), 7.72 (d, J=8.8 Hz, 2H), 7.78 (d, J=8.3 Hz, 1H).

1-methyl-4-(4-(pyrrolidin-1-yl)phenylsulfonyl)-1,2, 3,4-tetrahydroquinoxaline, 31

ESI/MS: m/z=358.26 [M+H]; $^1$H NMR (CDCl$_3$): 2.01-2.05 (m, 4H), 2.88 (t, J=5.5 Hz, 2H), 3.27-3.32 (m, 4H), 3.80 (t, J=5.5, 2H), 6.40 (d, J=9.1 Hz, 2H), 6.56-6.59 (m, 1H), 6.64-6.70 (m, 1H), 7.03-7.08 (m, 1H), 7.32 (d, J=9.1 Hz, 2H), 7.59-7.62 (m, 1H).

1-(4-(4,5-dihydro-1H-pyrazol-1-yl)phenylsulfonyl)-
4-methyl-1,2,3,4-tetrahydroquinoxaline, 32

ESI/MS: m/z=357.52 [M+H];
¹H NMR (CDCl₃): 2.88 (t, J=5.5 Hz, 2H), 3.01 (td, J=10.5 Hz and J=1.9 Hz, 2H), 3.69 (t, J=10.5, 2H), 3.82 (t, J=5.5, 2H), 6.55-6.58 (m, 1H), 6.65-6.71 (m, 1H), 6.88-6.91 (m, 3H), 7.03-7.09 (m, 1H), 7.36 (d, J=9.1 Hz, 2H), 7.59-7.63 (m, 1H).

1-(4-(1H-pyrazol-1-yl)phenylsulfonyl)-4-methyl-1,2,
3,4-tetrahydroquinoxaline, 33

ESI/MS: m/z=355.52 [M+H]
¹H NMR (CDCl₃): 2.65 (s, 3H), 2.92 (t, J=5.4, 2H), 3.88 (t, J=5.4, 2H), 6.51 (apparent s, 1H), 6.56 (d, J=8.3 Hz, 1H), 6.71 (t, J=7.7 Hz, 1H), 7.10 (t, J=8.3 Hz, 1H), 7.58 (d, J=8.8 Hz, 2H), 7.63 (d, J=8.0, 1H), 7.73 (d, J=8.8 Hz, 2H), 7.81 (d, J=8.3, 1H), 7.94 (d, J=2.5, 1H).

1-(4-(4-methyl-3,4-dihydroquinoxalin-1(2H)-ylsul-
fonyl)phenyl)pyrrolidin-3-ol, 34

ESI/MS: m/z=374.53 [M+H]
¹H NMR (CDCl₃): 2.01-2.13 (m, 1H), 2.43-2.53 (m, 1H), 3.60 (s, 3H), 3.68-3.86 (m, 2H), 4.07 (t, J=7.5 Hz, 1H), 7.14 (t, J=7.5 Hz, 1H), 7.35 (t, J=8.4 Hz, 2H), 7.61 (t, J=8.4 Hz, 2H).

1-(4-(4-methyl-3,4-dihydroquinoxalin-1(2H)-ylsul-
fonyl)phenyl)-3-(methylthiomethoxy)-1H-pyrrol-2
(5H)-one, 35

ESI/MS: m/z=446.6 [M+H]
¹H NMR (CDCl₃): 2.30 (s, 3H), 2.68 (s, 3H), 2.91 (t, J=5.8 Hz, 2H), 3.87 (t, J=5.5 Hz, 2H), 4.32 (d, J=2.5 Hz, 2H), 5.18 (s, 2H), 5.99 (t, J=2.5 Hz, 1H), 6.59 (d, J=8.8 Hz, 1H), 6.72 (td, J=8.8, 1.4 Hz, 1H), 7.10 (td, J=8.5, 1.3 Hz, 1H), 7.53 (d, J=9.1 Hz, 2H), 7.64 (dd, J=8.3, 1.4 Hz, 1H), 7.83 (d, J=8.9 Hz, 2H).

1-(4-(4-methyl-3,4-dihydroquinoxalin-1(2H)-ylsul-
fonyl)phenyl)pyrrolidine-2,3-dione, 36

ESI/MS: m/z=386.22 [M+H]

3-(dimethylamino)-1-(4-(4-methyl-3,4-dihydroqui-
noxalin-1(2H)-ylsulfonyl)phenyl)pyrrolidin-2-one,
37

ESI/MS: m/z=415.38 [M+H]

1-(4-(4-methyl-3,4-dihydroquinoxalin-1(2H)-ylsul-
fonyl)phenyl)pyrrolidin-3-one, 38

ESI/MS: m/z=372.54 [M+1-]
Prodrugs for Brain Cancer Use with compounds of Formula I.
Use of amino acid transporters, (i.e., L-type amino acid transporters (LAT), L-Valine (Val) or L-Leucine (Leu) ester prodrugs) improves solubility and allows for sulfonamide compounds to penetrate the blood brain barrier (BBB). Modification of the side chain hydroxyl group on the pyrrolidine or pyrrolidinone ring with O-benzylhydroxylamine or attaching an amidine or amidine-ester group to the side chain hydroxyl to give a zwitterionic species for improved BBB penetration or making a glucuronide or glucose (sugar) analog 3-gluco or 6-gluco analog to allow transport by glucose transporter (GLUT1) improves BBB penetration.

Example 3

Functional Activity of Compounds of Structure I

The potency of Wnt inhibition by several compounds of structure I using the above-described testing methods was determined. Approximately 50 sulfonamides were synthesized and tested. Table 1 lists the functional activity of some of the compounds of structure I in the Wnt inhibition assay.

TABLE 1[A]

Relative potency for Wnt inhibition by compounds of structure I.

| Compd # | Potency |
|---|---|
| MLG-III-53A | ++++ |
| 1 | +++ |
| 2 | ++++ |
| 3 | NA |
| 4 | ++++ |
| 5 | ++++ |
| 6 | +++ |
| 7 | ++++ |
| 8 | +++ |
| 9 | + |
| 11 | ++++ |
| 12 | ++++ |
| 13 | + |
| 14 | +++ |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | +++ |
| 31 | ++++ |
| 32 | ++++ |
| 33 | + |
| 34 | +++ |

[A]All the compounds were characterized by LRMS and/or ¹H NMR.
[B]Relative Wnt inhibition potency was based on compound IWR-1 possessing greatest inhibitory potency; +++++: >80% potency compared to IWR-1; ++++ between 60 to 80% potency compared to IWR-1; +++ between 40 to 60% potency compared to IWR-1; ++: <40% potency compared to compound IWR-1, + <20% potency compared to compound IWR-1.
NA, not available.

As observed from the data presented in Table 1, both free bases and salts gave significant Wnt inhibition potency. On the basis of the lipophilic character of many of the analogs, it is likely interaction site on the molecular target has a lipophilic character although polar interactions are apparent. To increase solubility, were possible, hydrochloride salts of the sulfonamides were synthesized. To afford appropriate bioavailability, sulfonamides were synthesized with chemical and metabolic stability in mind. As determined by HPLC, the chemical half life values of 1, 2, 6 and 7 was 120, 127, No change and 37 hours, respectively.

Example 4

Inhibition of Proliferation of Human Cancer Cell Lines by Compounds of Structure I We tested a subset of the 50 sulfonamide analogues for inhibition of proliferation of the MDA-MB-231, PC-3, MCF-7, and HCT-116 cancer cell lines. Following plating of the cells (24 hrs) in eight identical 96-well plates, the cells were treated with either Compound 1, 4, 15, or vehicle (DMSO) using a dose range of 1.6 to 5000 nM. After the lysis of cells, the cell lysate was resuspended in 25 μl PBS and the DNA was quantified using a PicoGreen assay by measuring fluorescence at $Ex_{490\ nm}/Em_{535\ nm}$. Cell proliferation was inhibited by Compounds 1, 4, and 15 for all the cancer cell lines tested with inhibition constants listed in Table 2.

TABLE 2

$IC_{50}$ values (nM) for inhibition of proliferation of several human cancer cell lines.

| | MDA-MB-231 | MCF-7 | PC-3 | HCT-116 |
|---|---|---|---|---|
| Compound 1 | 100 | 20 | 20 | 40 |
| Compound 4 | 250 | 40 | 100 | 100 |
| Compound 15 | 25 | 20 | 20 | 15 |

Example 5

Stimulation of Apoptosis of Several Cancer Cell Lines by Compounds of Structure I Given Compounds 1, 4, and 15 inhibited cancer cell proliferation, we tested whether compounds 1, 4, and 15 stimulated cancer cell apoptosis. The MDA-MB-231, MCF-7, PC-3, and HCT-116 cells were treated with the indicated compounds for 24 hrs. over a dose range from 1.6 to 5000 nM. Apoptosis was then measured by monitoring Caspase 3/7 cleavage (Caspase-Glo Kit). Compounds 1, 4, and 15 stimulated apoptosis of MDA-MB-231, MCF-7, PC-3, and HCT-116 with $EC_{50}$ values listed in Table 3.

TABLE 3

$IC_{50}$ values (nM) for stimulation of apoptosis of human cancer cell lines.

| Compound | PC-3 | HCT-116 |
|---|---|---|
| 1 | 49 | 96 |
| 4 | 117 | 143 |
| 15 | 32 | 15 |

Example 6

Decrease in Viability but not Acute Cytotoxicity of Several Cancer Cell Lines by Compounds of Structure I Given Compounds 1, 4, and 15 inhibited cancer cell proliferation and stimulated apoptosis, we tested the effects compounds 1, 4, and 15 on cancer cell viability and cytotoxicity. The MDA-MB-231, MCF-7, PC-3, and HCT-116 cells were treated with the indicated compounds for 24 hrs. over a dose range from 1.6 to 5000 nM. Viability and cytotoxicity were then measured by the Alamar Blue and Vibrant Cytotox assays respectively. Compounds 1, 4, and 15 decreased viability without cytotoxicity of MDA-MB-231, MCF-7, PC-3, and HCT-116 with $IC_{50}$ listed in Table 4. In addition, an Alamar Blue resazurin-based cell viability assay in HEK-293T cells showed 1 decreased cell viability with an $EC_{50}$ of ~25 nM but was not cytotoxic as measured by lack of leakage of G6PDH from HEK-293T cells.

TABLE 4

Viability and Cytotoxicity $IC_{50}$ values for 1, 4, and 15 in the indicated cancer cell lines.

| | Viability ($IC_{50}$, nM) | | | | Cytotoxicity ($IC_{50}$, nM) | | |
|---|---|---|---|---|---|---|---|
| Compound | PC-3 | LNCap | HCT-116 | MDA-MB-231 | LNCap | HCT-116 | MDA-MB-231 |
| 1 | 157 | 90 | 30 | 35 | >5000 | >5000 | >5000 |
| 4 | 17 | 87 | 52 | 45 | >5000 | >5000 | >5000 |
| 15 | 32 | 124 | 9 | 93 | >5000 | >5000 | >5000 |

Example 7

Figure 9:
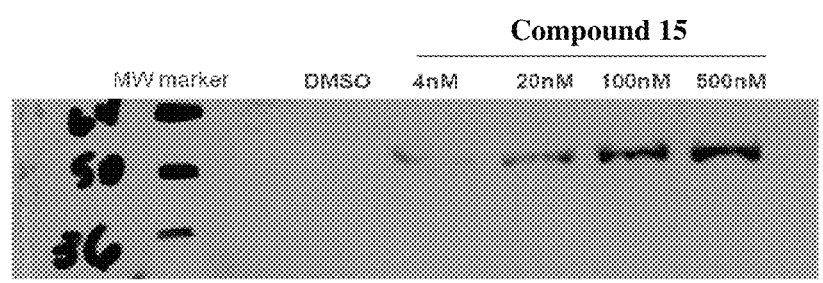
FIG. 9 shows that compound 15 increases p53 protein levels in a cancer cell.

Regulation of Wnt and Pro-Apoptotic Gene Expression of Several Cancer Cell Lines by Compounds of Structure I Given the effects of Compounds 1, 4, and 15 on biological functions (e.g., proliferation, viability, and apoptosis) in several cancer cell lines, we tested the effects of compounds 1, 4, and 15 on regulation of endogenous Wnt and pro-apoptotic gene expression. MDA-MB-231, MCF-7, PC-3, and HCT-116 cancerncells were treated with the indicated compounds for 24 hrs. over a dose range from 1.6 to 5000 nM. Gene expression was measured using qPCR, normalized to the housekeeping gene, 36B4, and calculated % change relative to DMSO control. NC, no change. Regulation of canonical Wnt and Apoptotic target genes, cMYC, CCND1, BAX, BAK, BBC3, FOS, and JUN was observed in the indicated cancer cells lines following treatment with sulfonamide analogs, 1, 4, and 15 as indicated in Table 5. The profile of gene regulation (induction or de-regulation) for the more potent compounds 4 and 15 is consistent with the compounds possessing potent anti-cancer potency.

on the stabilization of p53 protein, a major driver of apoptosis. HCT-116 cells were treated with Compound 15 for 24 hours using doses from 4 to 500 nM. Following preparation of whole cell extracts, equivalent total protein amounts were separated by SDS-PAGE and analyzed by Western Blot using an antibody to p53. As shown in FIG. 9, Compound 15 increased the stability of the p53 protein indicating an important role of p53 in the mechanism of action of compounds of structure I.

TABLE 5

Regulation of Wnt and Pro-apoptotic target genes by Compounds 1, 4 and 15.

| Treatments | | Endogenous Target Genes for Wnt & Apoptotic Pathways | | | | | | |
|---|---|---|---|---|---|---|---|---|
| Cell Line | Compound | MYC | CCDN1 | BAX | BAK | BBC3 | FOS | JUN |
| MDA-MB 231 | 1 | −70 | −72 | −70 | −42 | −78 | NC | −50 |
| | 4 | −55 | −25 | −65 | −50 | −80 | +100 | −45 |
| | 15 | −50 | −22 | −62 | −20 | −65 | −10 | −38 |
| MCF-7 | 1 | −25 | +50 | NC | −10 | −55 | −70 | +125 |
| | 4 | −5 | +100 | +75 | +25 | −40 | −85 | +50 |
| | 15 | −50 | +50 | −25 | +45 | +75 | −75 | +150 |
| LNCAP | 1 | −35 | −10 | −30 | −22 | −90 | −15 | NC |
| | 4 | −40 | −30 | −55 | −42 | −85 | −38 | NC |
| | 15 | −45 | −28 | −58 | −45 | −55 | −25 | +45 |
| PC-3 | 1 | +25 | +10 | +5 | −20 | −38 | +75 | +75 |
| | 4 | −75 | −42 | −55 | −55 | −37 | −25 | −25 |
| | 15 | −60 | −30 | −54 | −58 | −45 | −24 | −30 |
| HCT-116 | 1 | −45 | +40 | +5 | +75 | −80 | −70 | +525 |
| | 4 | −75 | −5 | NC | +110 | −90 | −85 | +725 |
| | 15 | −70 | +25 | −5 | +98 | −95 | −84 | +775 |

Example 8

In Vivo Efficacy of Compounds of Structure I

Figure 7:
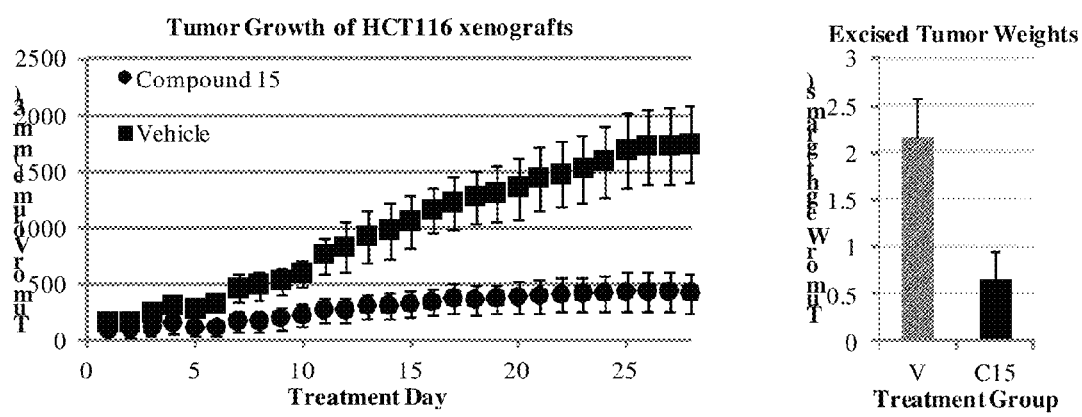
FIG. 7 shows that compound 15 decreases colon cancer in a xenograft study.
Figure 8:
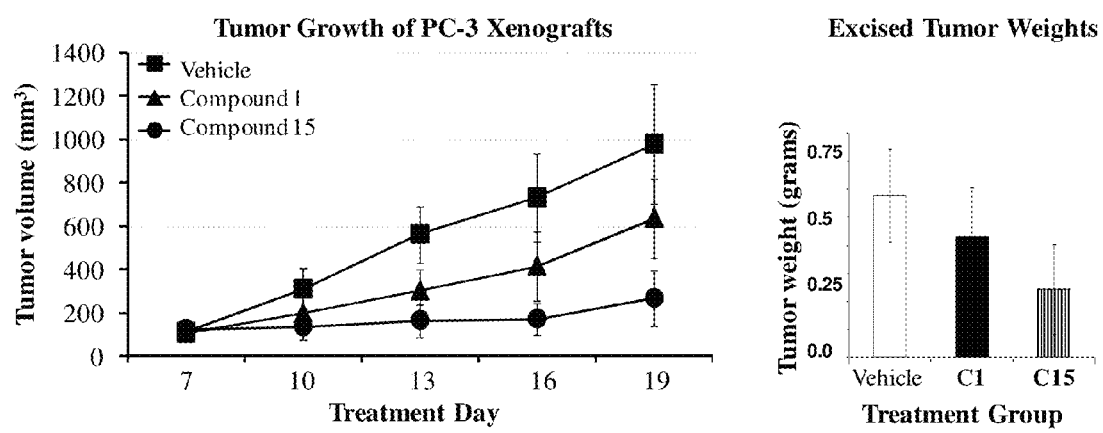
FIG. 8 shows that compounds 1 and 15 decrease prostate cancer in a xenograft study.

Based on the inhibition of cancer cell proliferation by the disclosed compounds the disclosed compounds likely will inhibit cancer cell migration. Given the effects Compounds 1, 4, and 15 on biological functions (i.e., proliferation, viability, and apoptosis) and likely inhibition of migration in several cancer cell lines, we tested the effects of compound 15 on growth of HCT-116 xenograft colon tumors in nu/nu mice. Following establishment of HCT-116 tumors, daily doses of either Compound 15 or vehicle were administered by i.p. injection at 20 mg/kg for 28 days. As shown in FIG. 7, Compound 15 decreased the growth of HCT-116 colon tumors. The weight of the excised HCT-116 tumors was 77% lower for the Compound 15-treated mice relative to the vehicle control on Day 28 of the experiment. Likewise, compound 1 and 15 inhibited the growth of PC-3 prostate tumors (FIG. 8). Following establishment of PC-3 tumors, daily doses of either Compounds 1, 15 or vehicle were administered by i.p. injection at 30 mg/kg for 19 days. Compound 15 was more potent 1 in good agreement with in vitro observations. The weight of the excised PC-3 tumors was 66% for compound 15-treated mice compared to vehicle-treated controls on Day 19 of the experiment. The data shows that 1 and 15 possess anti-cancer activity in an in vivo xenograft of human cancer.

Example 9

Stabilization of P53 Protein Levels by Compounds of Structure I

Given the effects Compounds 1, 4, and 15 on apoptosis in several cancer cell lines, we tested the effects of compound 15

Example 10

In Vivo Toxicitiy Assessment of Compounds of Structure I

Figure 10:
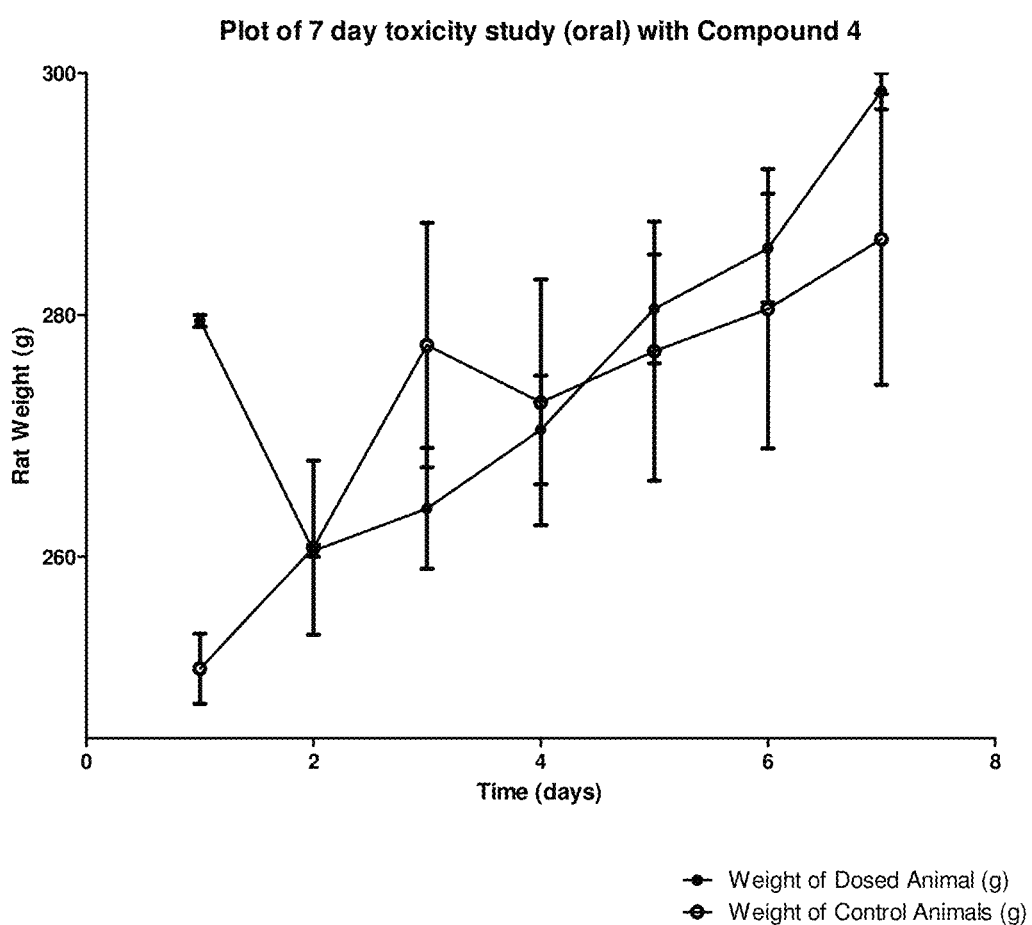
FIG. 10 shows the lack of in vivo toxicity for compound 4.
Figure 11:
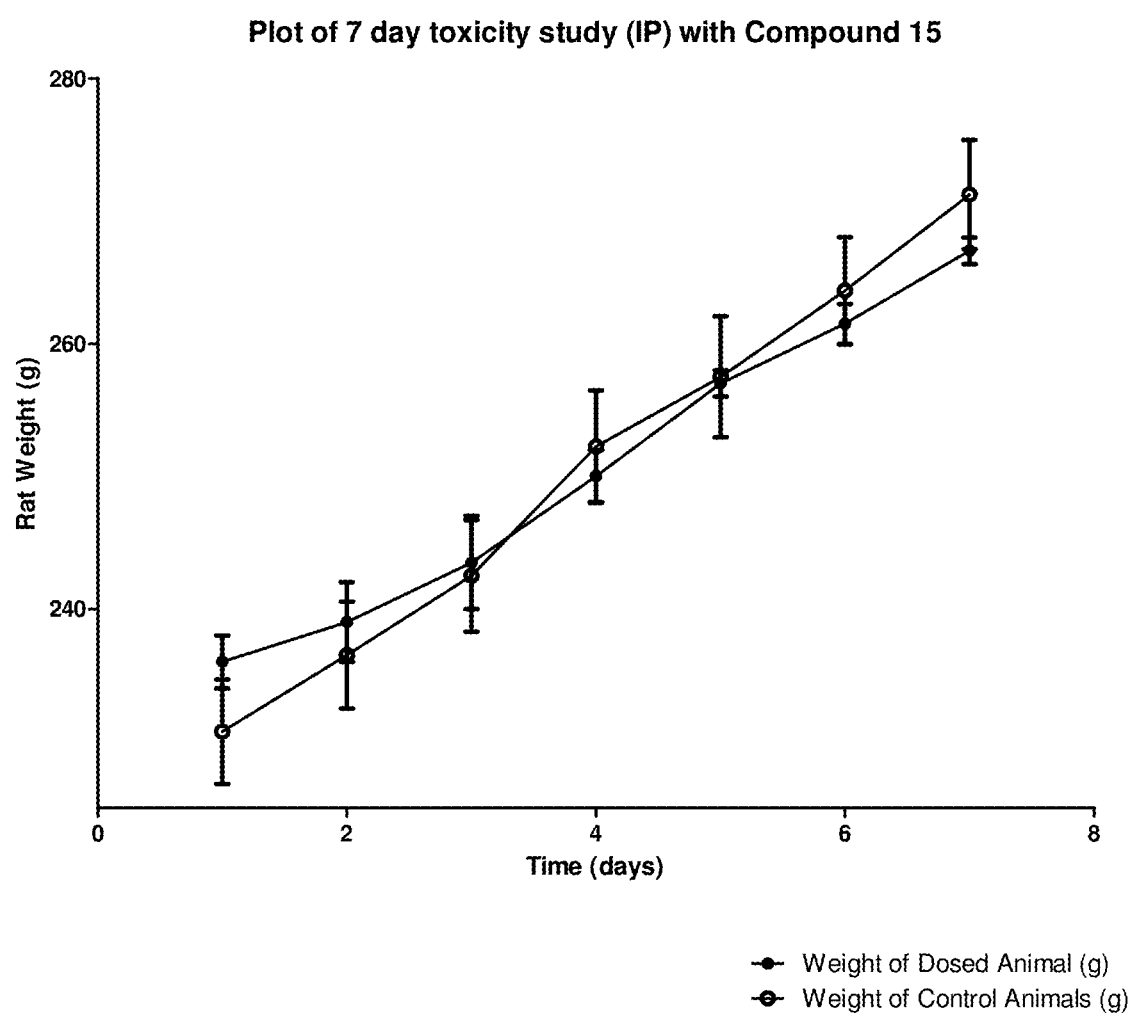
FIG. 11 shows the lack of in vivo toxicity for compound 15.

Compounds of structure I were designed to be chemically and metabolically stable and non-toxic. For example, the alpha methyl group of the quinoxalin ring system protects the sulfonamide from rapid metabolism or hydrolysis. Pharmacokinetics in rats bore this out as 31 had bioavailability of 11% and more polar analogs possessed bioavailability >60%. We tested Compounds 4 and 15 for toxicity in rats. In one study, we dosed rats with Compound 4 (p.o) daily for one week with 30 mg/kg. In another study, we dosed rats daily for one week with 30 mg/kg Compound 15 by p.o. administration. We monitored the weights of the rats daily over the course of both studies. As shown in FIGS. 10 and 11, no differences in the weights of the rats were observed for any of the treatments compared to controls. Additionally, no differences in food or water intake or behavior were noted during the course of the studies. Blood was also obtained from the animals at termination of the experiment. Serum clinical chemistry values showed that treatment with 15 did not alter the clinical chemistry values compared with vehicle-treated animals. Tissue taken from these animals (liver, heart, kidney, lung and intestine) also did not show any indication of toxicity. In addition, administration of 200 mg/kg to adult rats likewise did not show any indication of toxicity. Together, these data indicate Compounds 4 and 15 are nontoxic in healthy rats.

Example 11

Study of Natural Protein Inducers

Natural proteins that are dysregulated in cancer cells may provide important information about signaling pathways in cancer and provide insight into the dynamics of secreted pathway activators functioning during progression from normal cells to cancer cells.

It has been previously reported that normal Wnt are essential for many physiological processes. In contrast, a cell with dysfunctional Wnt pathway is associated with cell proliferation and cancer. Wnt antagonists, particularly Dickkopf 1 (Dkk) 1 activates the homeodomain protein Hex. Inhibition of canonical Wnt signaling far downstream from physiological processes may provide a selective means of interfering with cancer cell proliferation. The findings that Wnt inhibitors that inhibit TCF4 phosphorylation also inhibit several human cancers cell proliferation support the concept that factors operating in the far downstream portion of the Wnt pathway can provide a novel target for inhibition of various cancers including colon, prostate and breast cancer.

There have been no published screens for small molecule inhibitors of the Wnt pathway targeting TCF4. Compounds that have been described to inhibit the Wnt pathway appear to act earlier than the disclosure compounds.

Example 12

Study of Activities of Disclosure Compounds

Compounds were examined for potency to inhibit the Wnt pathway. FIGS. 2-4 shows that the compounds are functionally active.

The point of action is consistent with action of the disclosed compounds very distal in the Wnt pathway, working at TCF4.

To define the point of action in more detail, a more focused assay was designed to probe the activities of the compounds and showed that the disclosed compounds inhibited TCF4 phosphorylation.

To confirm that Wnt inhibition possessed physiological consequences, work with Xenopus showed that the disclosed compounds profoundly changed the morphology of Xenopus after exposure to the disclosed compounds.

Using colon cancer cell lines, it was shown that the disclosed compounds inhibited cancer cell proliferation.

The effect of the disclosure compounds on general cell toxicity showed that the compounds decreased cell viability but were not cytotoxic.

Signaling was tested using a standard luciferase response system for canonical Wnt/β-catenin/TCF signaling. Briefly, we used a cell line that had been transfected with a luciferase reporter gene under the control of the response element of a transcription factor that is activated by association with β-catenin and is the target of canonical Wnt signaling. Using this assay, the disclosed compounds inhibited the endogenous Wnt pathway as determined by a decrease in mRNA levels of canonical Wnt target genes, Cyclin D1 (CCND1), Axin2 (AXIN2), and c-Myc (c-MYC) in both HEK293T and SW480 colorectal cells indicating that they act on signals that converge on the pathway to decrease Wnt activity.

To summarize, using a number of assays based on reporter cell lines, a distinct chemical classes of sulfonamide molecules were identified, as discussed above. They were found to act in the far downstream portion of the Wnt signaling pathway. Results suggested that the disclosed compounds inhibit Wnt signaling, but do not themselves interfere with normal physiological upstream Wnt pathway function.

In summary, each series of compounds appeared to inhibit Wnt pathway. Based on the initial "hit," a sulfonamide, approximately 50 analogs were synthesized that provided a drug-like "smart library" with various new chemical substituents. Some of the results are provided in some of the above Examples. The analogs were tested in the Wnt assay described above and the results showed a structure-activity relationship (SAR) for the "smart library". Several of the synthetic analogs showed increased potency (i.e., $IC_{50}$ values in the low nM range) and possessed greater drug-like properties.

For refined, more potent sulfonamides, over 20 analogs of that class were synthesized, tested in the Wnt assay and the data also described an SAR for this second drug-like "smart library."

Small scale transcriptional profiling of typical cancer cell markers suggested that sulfonamides inhibited the Wnt target genes that may be responsible for cancer cell proliferation. In conclusion, these classes of small molecules act by inhibiting the Wnt pathway at a distal point in the pathway at a novel target TCF4.

The disclosed compounds induce a morphology change from a flat adherent cell to a rounded non-adherent one in cancer cells with wild-type and mutant p53 (colon, HCT-116 and breast, MCF-7) after cancer cells were treated with Compounds 1, 4, or 15 at 500 nM for 24 hours. Using the same treatment conditions, this morphology change was not observed in 10.1 cells lacking p53 (i.e., -/- p53, isogenic HCT-116 cells) highlighting the integral importance of p53 protein in the mechanism of action of the disclosed compounds.

The disclosed compounds activate p53 transcriptional activity as measured by a p53-luciferase reporter assay. Further, the potency of activation of p53 transcriptional activity and the potency of inhibition of Wnt transcriptional activity show similar trends as indicated by testing of six of the disclosed compounds in both assays simultaneously and then comparing the $EC_{50s}$ and $IC_{50s}$, respectively with very large correlation coefficients ($r^2 > 0.8$). Thus, Compound 15 potently activates p53 transcription ($EC_{50}$++++) and potently inhibits Wnt transcriptional activity ($IC_{50}$++++).

Although the disclosure has been described with reference to the above examples, it will be understood that modifications and variations are encompassed within the spirit and scope of the disclosure. Accordingly, the disclosure is limited only by the following claims.

What is claimed is:

1. A compound of Formula I:

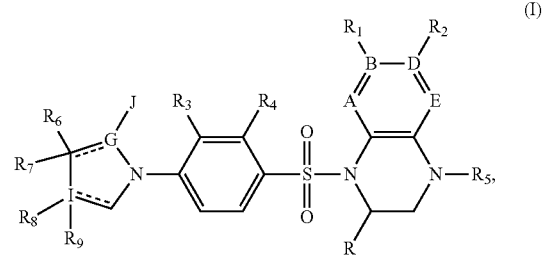

or a pharmaceutically acceptable salt or N-oxide thereof, wherein:

A, B, D and E are each independently C or N;

G and I are selected from the group consisting of C, N, O and S; and

R, $R^1$, $R^2$, $R^3$, $R^4$, $R^5$, $R^6$, $R^7$ and $R^8$ are independently H, alkyl, aryl, halo, —O-alkyl, O-aryl, N-alkyl, N,N-dialkyl, N-aryl, N,N-diaryl, cycloalkyl, cycloheteroalkyl or heteroaryl, or $R^6$ and $R^7$ together are oxo and $R^1$-$R^5$, and $R^8$ and $R^9$ are as defined herein or $R^8$ and $R^9$ together are oxo, or $R^8$ and $R^9$ are oxo and $R^1$-$R^7$ are as defined herein or $R^1$-$R^5$ are as defined and $R^7$ and $R^8$ together are oxo; and J is oxo, —H, $C_1$-$C_6$ alkyl, aryl, —OH, cycloalkyl, cyclo-heteroalkyl or heteroaryl, provided when:

the optional double bonds are present, G and I independently are C or N, one of $R^6$, $R^7$ and one of $R^8$, $R^9$ is absent and the others are as defined herein, and J is other than oxo, or is absent or otherwise forming a salt when G is N, or the optional double bond to G is present and the double bond to I is absent, G is C or N, one of $R^6$, $R^7$ is absent and the other is as defined herein, $R^8$ and $R^9$ are as defined herein with one of $R^8$ and $R^9$ absent or otherwise forming a salt when I is N or both are absent when I is O or S or otherwise forming a salt when I is S; and J is other than oxo, or is absent or otherwise forming a salt when G is N, or the optional double bond to I is present and the double bond to G is absent, I is C or N, one of $R^8$, $R^9$ is absent and the other is as defined herein, and forming a salt when I is N; and J is absent when G is O or S or otherwise forming a salt when G is S.

2. The compound of claim 1 wherein the compound of Formula I is

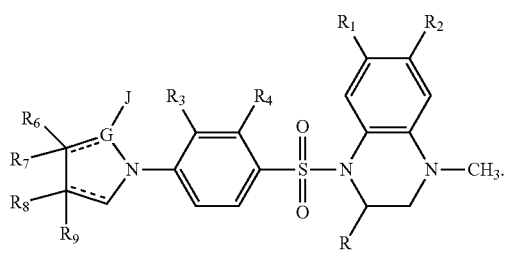

3. The compound of claim 2, wherein the compound of Formula I is selected from the group consisting of:

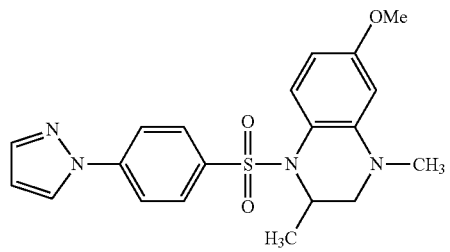

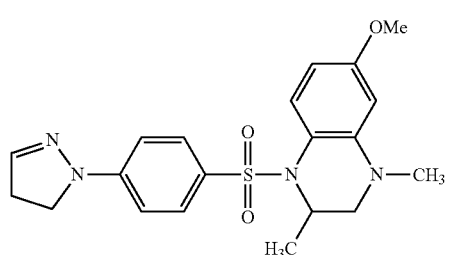

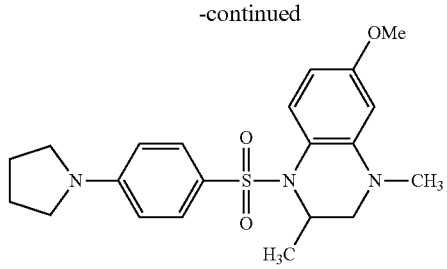

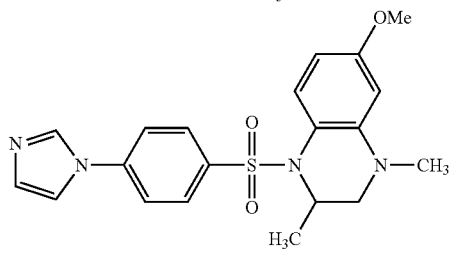

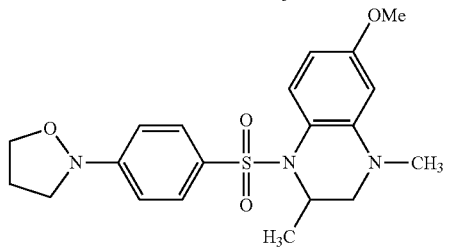

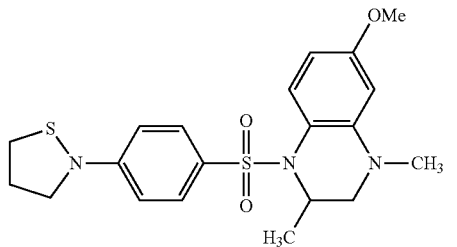

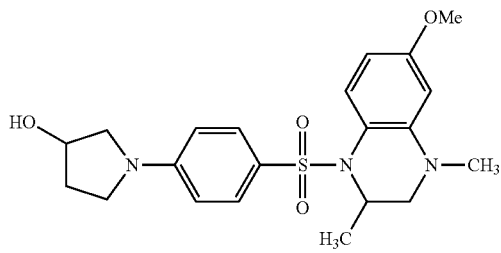

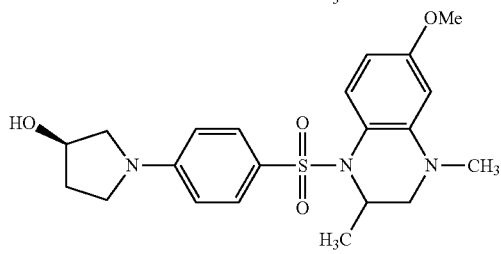

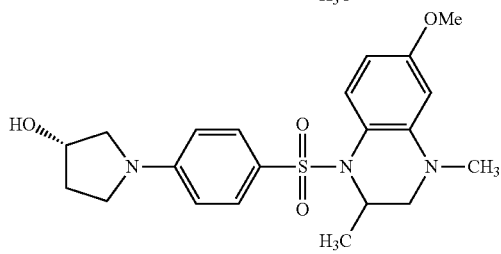

-continued
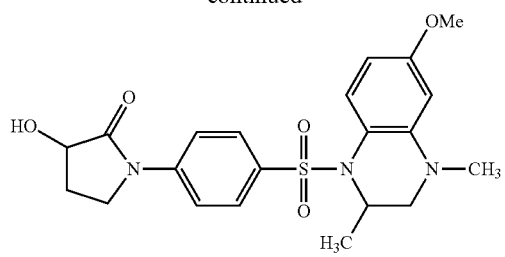
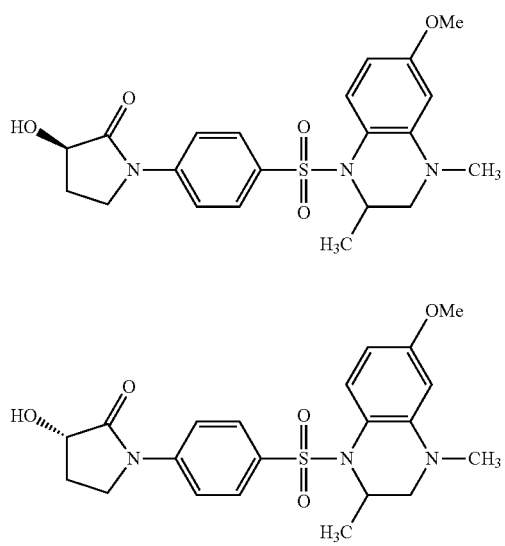
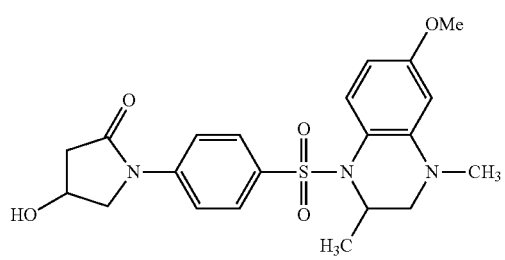
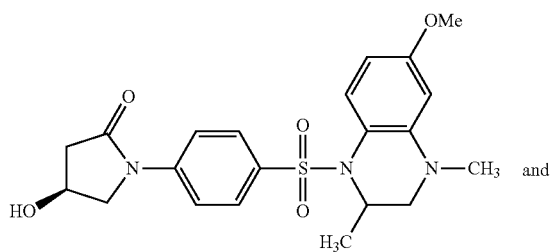
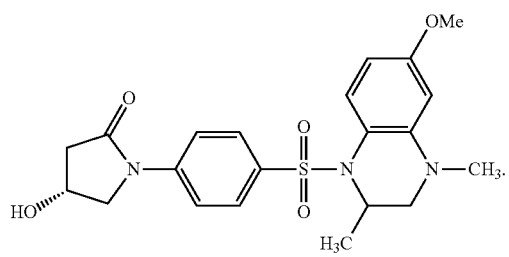
4. The compound of claim 2, wherein the compound of Formula I is a compound of Formula IA:
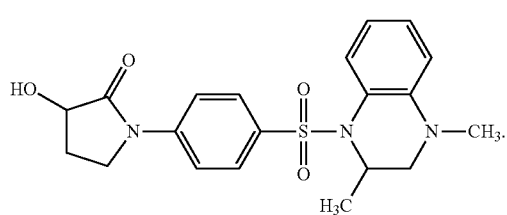
(Formula IA)
5. The compound of claim 2, wherein the compound of Formula I is a compound of Formula IB:
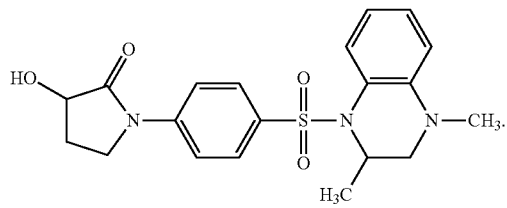
(Formula IB)
6. A compound of claim 2, wherein the compound of Formula I is selected from the group consisting of:
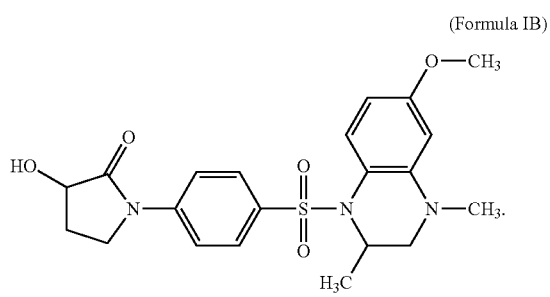 [SMILES: COc1ccc2c(c1)N(C)CC(C)N2S(=O)(=O)c1ccc(N2CCC(O)C2=O)cc1]
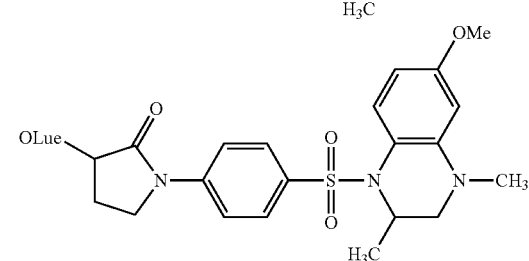
and
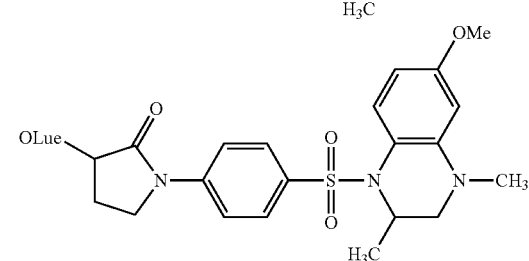
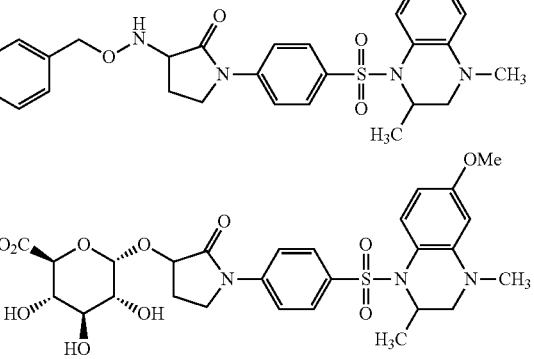

43
-continued
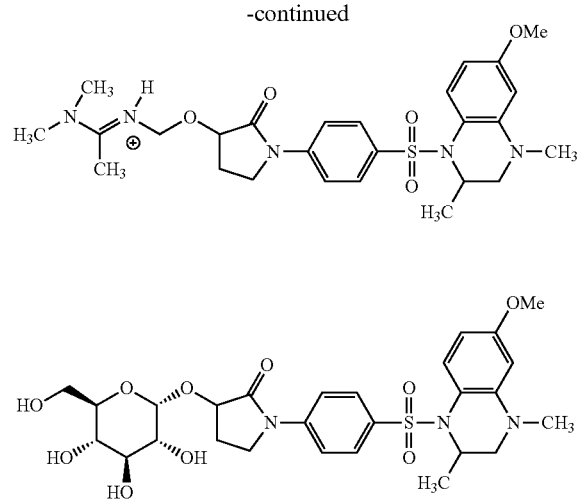
44
-continued
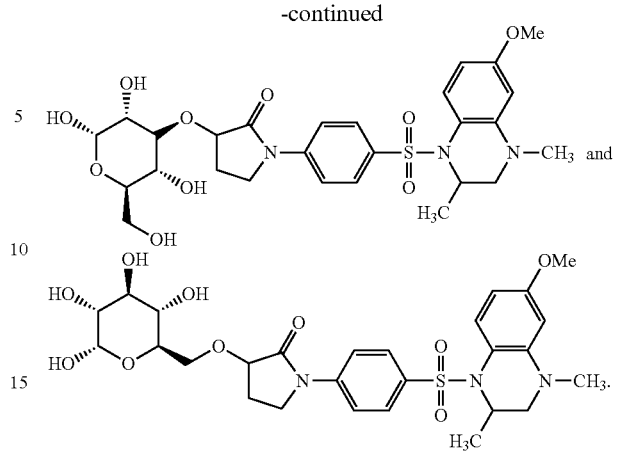
* * * * *